(12) United States Patent
Susi

(10) Patent No.: US 9,861,743 B2
(45) Date of Patent: *Jan. 9, 2018

(54) SYSTEM AND METHOD FOR COMMUNICATION WITH AN INFUSION DEVICE

(71) Applicant: IRadimed Corporation, Winter Park, FL (US)

(72) Inventor: Roger E. Susi, Winter Park, FL (US)

(73) Assignee: IRADIMED CORPORATION, Winter Springs, FL (US)

( * ) Notice: Subject to any disclaimer, the term of this patent is extended or adjusted under 35 U.S.C. 154(b) by 892 days.

This patent is subject to a terminal disclaimer.

(21) Appl. No.: 13/955,354

(22) Filed: Jul. 31, 2013

(65) Prior Publication Data

US 2014/0100519 A1   Apr. 10, 2014

Related U.S. Application Data

(63) Continuation of application No. 13/361,750, filed on Jan. 30, 2012, now Pat. No. 8,500,694, which is a
(Continued)

(51) Int. Cl.
*A61M 5/172* (2006.01)
*A61M 5/142* (2006.01)
(Continued)

(52) U.S. Cl.
CPC ........ *A61M 5/172* (2013.01); *A61M 5/14228* (2013.01); *A61M 5/16831* (2013.01);
(Continued)

(58) Field of Classification Search
CPC .......... A61M 5/14228; A61M 5/16831; A61M 5/16854; A61M 5/16877; A61M 5/172;
(Continued)

(56) References Cited

U.S. PATENT DOCUMENTS 2,696,963 A   12/1954   Shepherd
4,221,224 A    9/1980   Clark
(Continued)

FOREIGN PATENT DOCUMENTS

DE   19714711 A1   10/1998
EP   0 447 985 A    9/1991
(Continued)

OTHER PUBLICATIONS

Sashida, Toshiiku et al., An Introduction to Ultrasonic Motors, Oxford Science Publications, 1993, Selected Pages, 90 pages total.

*Primary Examiner* — Kami A Bosworth
(74) *Attorney, Agent, or Firm* — Knobbe Martens Olson & Bear LLP

(57) ABSTRACT

It may be desirable to monitor or control a pump remotely. For example, the pump may be positioned near the patient, with remote control or monitoring of the pump occurring in a control room. In one exemplary embodiment, the pump is used in an MRI environment. In another exemplary embodiment, the pump is used in a hyperbaric chamber. The pump may monitor one or more physiological parameters and transmit them to the remote. The pump may also transmit information relating to the pump's operation. The pump may send the device and/or physiological data using one or more packets. The packets may consist of low priority sequential packets and high-priority asynchronous packets. The high-priority packets may enable the real-time monitoring of a patient's heart beat or other physiological parameter.

20 Claims, 21 Drawing Sheets

Related U.S. Application Data continuation of application No. 12/172,906, filed on Jul. 14, 2008, now Pat. No. 8,105,282.

(60) Provisional application No. 60/949,812, filed on Jul. 13, 2007.

(51) Int. Cl.
   *A61M 5/168* (2006.01)
   *A61M 5/36* (2006.01)

(52) U.S. Cl.
   CPC ......... *A61M 5/16854* (2013.01); *A61M 5/365* (2013.01); *A61M 2205/3306* (2013.01); *A61M 2205/3375* (2013.01); *A61M 2205/3561* (2013.01); *A61M 2205/3592* (2013.01)

(58) Field of Classification Search
   CPC ........... A61M 2005/14208; A61M 2205/3553; A61M 2205/3561; A61M 2205/3569; A61M 2205/3576; A61M 2205/3584; A61M 2205/3592; A61M 2205/3334; A61M 2205/3375
   See application file for complete search history.

(56) References Cited

U.S. PATENT DOCUMENTS

| | | | |
|---|---|---|---|
| 4,344,743 A | 8/1982 | Bessman et al. | |
| 4,457,751 A | 7/1984 | Rodler | |
| 4,460,358 A | 7/1984 | Somerville et al. | |
| 4,564,812 A | 1/1986 | Van Dijk | |
| 4,689,043 A | 8/1987 | Bisha | |
| 4,798,590 A | 1/1989 | O'Leary | |
| 4,857,048 A | 8/1989 | Simons et al. | |
| 4,888,514 A | 12/1989 | Takahashi et al. | |
| 5,017,192 A | 5/1991 | Dodge et al. | |
| 5,021,700 A | 6/1991 | Takahashi et al. | |
| 5,041,132 A | 8/1991 | Miyata | |
| 5,059,173 A | 10/1991 | Sacco | |
| 5,097,829 A | 3/1992 | Quisenberry | |
| 5,130,619 A | 7/1992 | Izuno | |
| 5,149,030 A | 9/1992 | Cockrill | |
| 5,181,910 A | 1/1993 | Scanlon | |
| 5,290,239 A | 3/1994 | Classey et al. | |
| 5,401,256 A | 3/1995 | Stone et al. | |
| 5,437,635 A | 8/1995 | Fields et al. | |
| 5,494,036 A | 2/1996 | Uber et al. | |
| 5,522,799 A | 6/1996 | Furukawa | |
| 5,553,619 A | 9/1996 | Prince | |
| 5,563,464 A | 10/1996 | Okubo et al. | |
| 5,609,575 A | 3/1997 | Larson et al. | |
| 5,644,199 A | 7/1997 | Nojima et al. | |
| 5,713,856 A | 2/1998 | Eggers et al. | |
| 5,770,181 A | 6/1998 | Kirkland | |
| 5,772,635 A | 6/1998 | Dastur et al. | |
| 5,864,331 A | 1/1999 | Anand et al. | |
| 5,865,797 A | 2/1999 | Zeeman | |
| 5,967,484 A | 10/1999 | Morris | |
| 5,984,862 A | 11/1999 | Honda | |
| 6,052,614 A | 4/2000 | Morris et al. | |
| 6,078,273 A | 6/2000 | Hutchins | |
| 6,102,678 A | 8/2000 | Peclat | |
| 6,117,115 A | 9/2000 | Hill et al. | |
| 6,193,480 B1 | 2/2001 | Butterfield | |
| 6,198,285 B1 | 3/2001 | Kormos et al. | |
| 6,213,723 B1 | 4/2001 | Danby et al. | |
| 6,221,045 B1 | 4/2001 | Duchon et al. | |
| 6,230,041 B1 | 5/2001 | Prince | |
| 6,240,311 B1 | 5/2001 | Prince | |
| 6,243,600 B1 | 6/2001 | Prince | |
| 6,248,093 B1* | 6/2001 | Moberg | A61M 5/1456 128/DIG. 12 |
| 6,261,262 B1 | 7/2001 | Briggs et al. | |
| 6,213,738 B1 | 10/2001 | Danby et al. | |
| 6,213,739 B1 | 10/2001 | Phallen et al. | |
| 6,316,862 B1 | 11/2001 | Nakata et al. | |
| 6,371,732 B1 | 4/2002 | Moubayed | |
| 6,406,426 B1* | 6/2002 | Reuss | A61M 5/1723 128/903 |
| 6,418,337 B1 | 7/2002 | Torchia et al. | |
| 6,443,318 B2 | 10/2002 | Prince | |
| 6,503,221 B1 | 1/2003 | Briggs et al. | |
| 6,516,749 B1* | 2/2003 | Salasidis | A61B 5/1118 119/421 |
| 6,619,051 B1 | 9/2003 | Kilawee et al. | |
| 6,629,955 B2 | 10/2003 | Morris | |
| 6,635,033 B1 | 10/2003 | Hill et al. | |
| 6,641,562 B1 | 11/2003 | Peterson | |
| 6,643,537 B1 | 11/2003 | Zatezalo et al. | |
| 6,659,978 B1 | 12/2003 | Kasuga et al. | |
| 6,685,668 B1 | 2/2004 | Cho et al. | |
| 6,749,591 B1 | 6/2004 | McNally et al. | |
| 6,848,444 B2 | 2/2005 | Smith et al. | |
| 6,881,043 B2 | 4/2005 | Barak | |
| 6,889,072 B2 | 5/2005 | Prince | |
| 6,893,414 B2 | 5/2005 | Goble et al. | |
| 7,044,960 B2 | 5/2006 | Vorhees | |
| 7,103,419 B2 | 9/2006 | Engleson et al. | |
| 7,226,430 B2 | 6/2007 | Ludin | |
| 7,267,661 B2 | 9/2007 | Susi | |
| 7,315,109 B1 | 1/2008 | Griffiths et al. | |
| 7,384,410 B2 | 6/2008 | Eggers et al. | |
| 7,404,809 B2 | 7/2008 | Susi | |
| 7,414,404 B2 | 8/2008 | Keene | |
| 7,489,128 B2 | 2/2009 | Kopp | |
| 7,545,140 B2 | 6/2009 | Humphreys et al. | |
| 7,553,135 B2 | 6/2009 | Cho et al. | |
| 7,553,295 B2 | 6/2009 | Susi | |
| 7,611,498 B2 | 11/2009 | Hasler | |
| 7,753,882 B2 | 7/2010 | Susi | |
| 8,105,282 B2 | 1/2012 | Susi et al. | |
| 8,148,989 B2 | 4/2012 | Kopp | |
| 8,150,493 B2 | 4/2012 | Susi | |
| 8,262,642 B2 | 9/2012 | Susi | |
| 8,308,452 B2 | 11/2012 | Amirouche et al. | |
| 8,378,836 B2 | 2/2013 | Kopp et al. | |
| 8,469,932 B2 | 6/2013 | Susi | |
| 8,500,694 B2 | 8/2013 | Susi | |
| 8,690,829 B2 | 4/2014 | Susi | |
| 9,072,577 B1 | 7/2015 | Ferko, III | |
| 9,198,584 B2 | 12/2015 | Yamashita et al. | |
| 9,585,574 B2 | 3/2017 | Nelson | |
| 2001/0014286 A1 | 8/2001 | Peters | |
| 2002/0017299 A1 | 2/2002 | Hickle | |
| 2002/0025255 A1 | 2/2002 | Wright et al. | |
| 2002/0038392 A1* | 3/2002 | De La Huerga | A61M 5/14212 710/8 |
| 2002/0115933 A1 | 8/2002 | Duchon et al. | |
| 2002/0165503 A1 | 11/2002 | Morris et al. | |
| 2002/0181866 A1 | 12/2002 | Crook et al. | |
| 2003/0014035 A1 | 1/2003 | Trombley et al. | |
| 2003/0050555 A1 | 3/2003 | Critchlow et al. | |
| 2003/0058502 A1 | 3/2003 | Griffiths et al. | |
| 2003/0171670 A1 | 9/2003 | Gumb et al. | |
| 2004/0024434 A1 | 2/2004 | Yang et al. | |
| 2004/0030233 A1 | 2/2004 | Frazier et al. | |
| 2004/0122486 A1 | 6/2004 | Stahmann et al. | |
| 2004/0167465 A1 | 8/2004 | Mihai et al. | |
| 2004/0176984 A1 | 9/2004 | White et al. | |
| 2004/0179217 A1 | 9/2004 | Chapman | |
| 2004/0225341 A1 | 11/2004 | Schock | |
| 2004/0249344 A1 | 12/2004 | Nemoto | |
| 2005/0017910 A1 | 1/2005 | Park | |
| 2005/0139002 A1 | 6/2005 | Onishi | |
| 2005/0256388 A1 | 11/2005 | Susi | |
| 2005/0261563 A1 | 11/2005 | Zhou et al. | |
| 2006/0042633 A1 | 3/2006 | Bishop et al. | |
| 2006/0085043 A1 | 4/2006 | Stevenson | |
| 2006/0160491 A1 | 7/2006 | Eberhart | |
| 2006/0173406 A1* | 8/2006 | Hayes | A61B 5/14532 604/67 |
| 2006/0173412 A1 | 8/2006 | Susi | |
| 2006/0224141 A1 | 10/2006 | Rush et al. | |

(56) References Cited

U.S. PATENT DOCUMENTS

| | | |
|---|---|---|
| 2006/0229551 A1 | 10/2006 | Martinez et al. |
| 2006/0231238 A1 | 10/2006 | Ball |
| 2007/0049983 A1 | 3/2007 | Freeberg |
| 2007/0135797 A1* | 6/2007 | Hood ............... A61K 9/0004 604/892.1 |
| 2007/0179434 A1 | 8/2007 | Weinert et al. |
| 2008/0004567 A1 | 1/2008 | Susi |
| 2008/0312512 A1* | 12/2008 | Brukalo ............... A61B 5/0002 600/300 |
| 2008/0312584 A1* | 12/2008 | Montgomery ...... A61M 5/14244 604/67 |
| 2008/0312585 A1* | 12/2008 | Brukalo ............ A61M 5/14244 604/67 |
| 2009/0157004 A1 | 6/2009 | Susi |
| 2009/0264857 A1 | 10/2009 | Susi |
| 2010/0331667 A1 | 12/2010 | Nelson |
| 2011/0009733 A1 | 1/2011 | Susi |
| 2013/0281966 A1 | 10/2013 | Susi |
| 2015/0023821 A1 | 1/2015 | Campbell et al. |
| 2015/0374537 A1 | 12/2015 | Susi |
| 2016/0131788 A1 | 5/2016 | Kopp |

FOREIGN PATENT DOCUMENTS

| | | |
|---|---|---|
| EP | 0 602 635 A1 | 6/1994 |
| EP | 0 606 099 A2 | 7/1994 |
| EP | 1 226 839 A1 | 7/2003 |
| JP | 05-084296 | 4/1993 |
| JP | 07-059851 | 3/1995 |
| JP | 07-059853 | 3/1995 |
| JP | 7-178169 | 7/1995 |
| JP | 08-033367 | 2/1996 |
| JP | 08-126627 | 5/1996 |
| JP | 11-148462 | 6/1999 |
| JP | 2001-104478 | 4/2001 |
| WO | WO 95/22999 | 8/1995 |
| WO | WO 02/00276 A1 | 1/2002 |
| WO | WO 03/105925 A2 | 12/2003 |
| WO | WO 2005/026544 | 3/2005 |
| WO | WO 2009/087714 | 7/2009 |

* cited by examiner

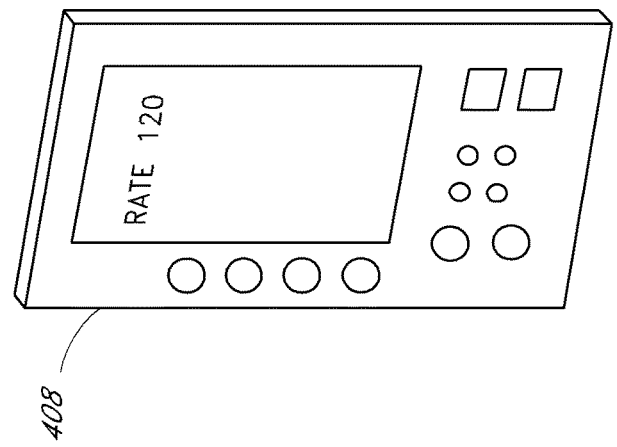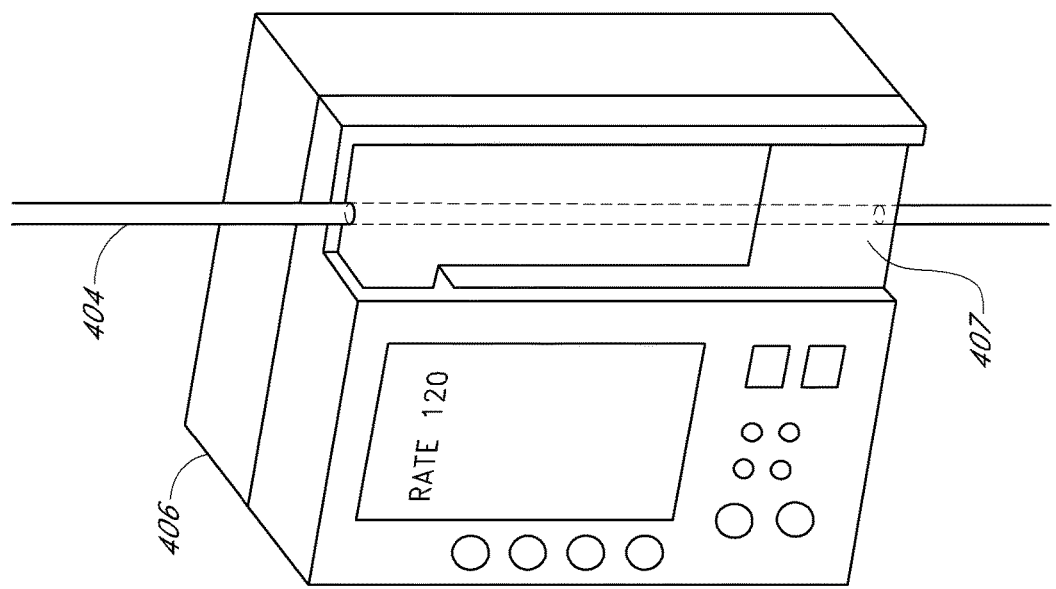
FIG. 4

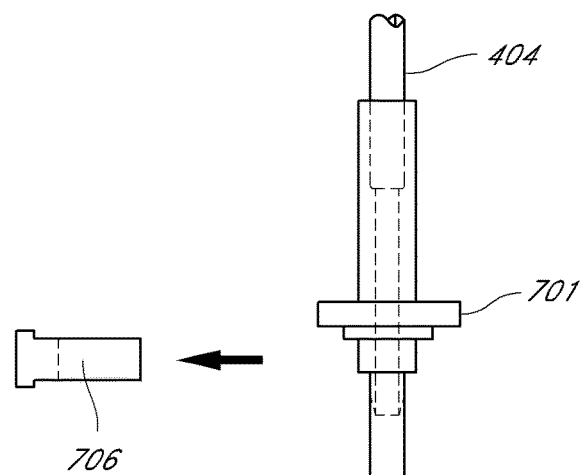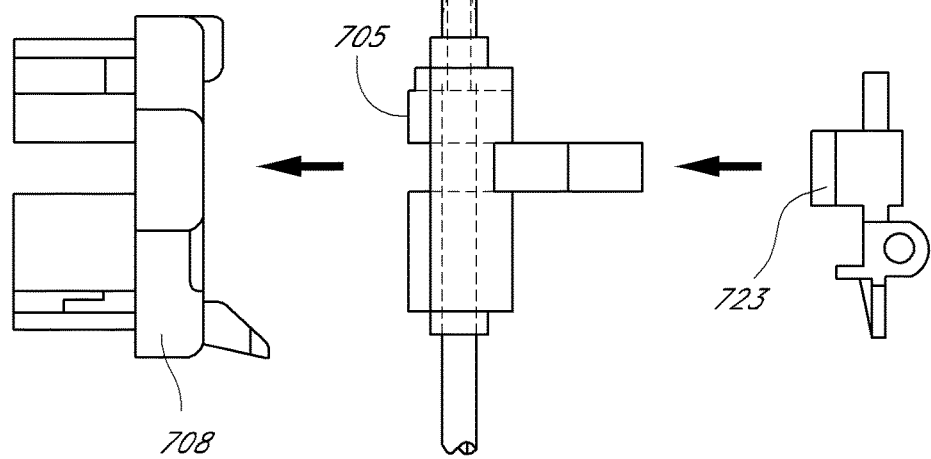
FIG. 6

← FIG. 12A    FIG. 12C →

SYSTEM AND METHOD FOR COMMUNICATION WITH AN INFUSION DEVICE

RELATED APPLICATIONS

This application is a continuation of U.S. patent application Ser. No. 13/361,750, filed Jan. 30, 2012 which is a continuation of U.S. patent application Ser. No. 12/172,906, filed Jul. 14, 2008, now U.S. Pat. No. 8,105,282, which claims priority to U.S. Provisional 60/949,812, filed Jul. 13, 2007, the entirety of each of which is hereby incorporated by reference herein and made a part of the present specification.

FIELD OF THE INVENTION

This invention relates to a system and method for remotely communicating with an infusion device.

BACKGROUND

It is desirable to control the intravenous (IV) administration of liquids to a patient. Frequently, patients scheduled for MRI examination arrive with IV solutions being administered and controlled by devices which must be disconnected as the patient is moved into the suite where high magnetic fields are present and no outside RF interference can be tolerated. Patients receiving hyperbaric chamber treatments may also need administration of IV solutions. Hyperbaric chambers may treat multiple patients at a time, and it is undesirable to stop hyperbaric treatment if a change in the administration of IV solution is needed.

SUMMARY

It may desirable to monitor or control a pump remotely. For example, the pump may be positioned near the patient, with remote control or monitoring of the pump occurring in a control room. In one exemplary embodiment, the pump is used in an MRI environment. In another exemplary embodiment, the pump is used in a hyperbaric chamber.

In one embodiment, the remote utilizes controls that mirror the controls located on the pump. For example, the remote controls may include the start or stop of fluid flow, silence of alarms, or setting or titrating a fluid delivery rate or volume. It should be understood that the controls on the remote are not necessarily coextensive with the controls on the pump.

In one embodiment, the display on the remote may also mirror the display located on the pump. For example, the remote may display alarm conditions or the status of the battery at the pump. Again, the information displayed on the remote is not necessarily coextensive with the information displayed on the pump.

In one embodiment, controls at the remote and the pump may be operated simultaneously.

In one embodiment, the remote acts as a charger for a spare pump battery. The charge status of the spare battery may be displayed by the remote.

In one embodiment, a side car module is attached to the pump to provide a second channel for infusion delivery. The remote allows for controlling both channels.

In one embodiment, the pump operates without the remote or if communication between the remote and the pump is interrupted. Displays on the pump and remote may indicate the connection status and relative signal level. The remote may provide an alarm if the connection is interrupted.

In one embodiment, the remote uses selectable communication channels. For example, a remote may be used to communicate with more than one pump. Similarly, multiple remote/pump pairings may be used in the same vicinity.

In one embodiment, the infusion device includes an ultrasonic motor that eliminates magnetic materials and that does not produce any detrimental magnetic fields and that is not affected by external magnetic fields. The ultrasonic motor may drive a peristaltic or other suitable fluid pumping mechanism. The motor may be driven by a multiphasic electronic signal with little RF harmonic noise in the spectral range of about 6 or 8 MHz to about 130 MHz in which MRI receivers are most sensitive. The drive power for the ultrasonic motor is generated via circuitry which produces multiphasic drive signals of at least sine and cosine waveforms at related ultrasonic frequencies. These drive signals are produced as a sinusoidal wave to reduce high frequency harmonic components which may disturb RF responsiveness. One scheme for producing these multiphasic signals uses coreless or "Air Core" transformers constructed with inherent leakage inductance that interacts with the complex impedance of the ultrasonic motor to convert lower voltage square wave signals at the primary winding into sinusoidal high voltage signals at the secondary windings suitable for powering the ultrasonic motor and producing little harmonic RF interference. Alternatively, D.C. voltages of opposite polarities can be alternately switched to supply alternating voltages. The switched signals can be filtered into sinusoidal signals and applied to the inputs of high voltage linear amplifiers that are set for such gain as needed to produce resultant outputs of sufficient voltage and sinusoidal shape to drive the ultrasonic motor.

Control electronics receive commands through an input keypad for setting prescribed fluid flow rates to be delivered, and such inputs are translated into signals to control the ultrasonic motor and pumping mechanism. Various safety devices feed back operational information to the control electronics, including detection of motor speed and motion of pump elements, air bubbles in the fluid path, drip rate, high pressure, low fluid, low/no flow, overtime, and the like. The present infusion device includes battery power for portability, and is housed in one RF-shielded, non-magnetic housing to prevent introducing image degrading RF interference or producing distortions of the homogeneous magnetic field, and without being affected by the strong magnetic fields or RF energy produced by the MRI system.

In one embodiment, the infusion device may be configured to monitor one or more physiological parameters of a patient. In one embodiment, the infusion device may be configured to transmit information related to its operation. In one embodiment, the physiological parameter and/or device operation information may be transmitted to a remote using a series of packets. In one embodiment, the packets may include a first category of packets sent in a prescribed sequence. In one embodiment, the first category of packets is sent at predetermined intervals. In one embodiment, the first category of packets has a guaranteed minimum rate of transmission. In one embodiment, the packets may also include a second category of packets corresponding to high-priority data. In one embodiment, the infusion device may be configured to interleave packets containing high-priority data into the prescribed sequence of category one packets. In one embodiment, the remote or controller receiving the packets may utilize a checksum or other appropriate means to verify the packets' integrity. In one embodiment, category two packets may be used to enable substantially real-time monitoring of a patient's heart beat.

BRIEF DESCRIPTION OF THE DRAWINGS

FIG. 4 is a partial perspective view of one embodiment of a pumping apparatus.

FIG. 6 is a side view of a length of precision tubing.

DETAILED DESCRIPTION

Figure 1:
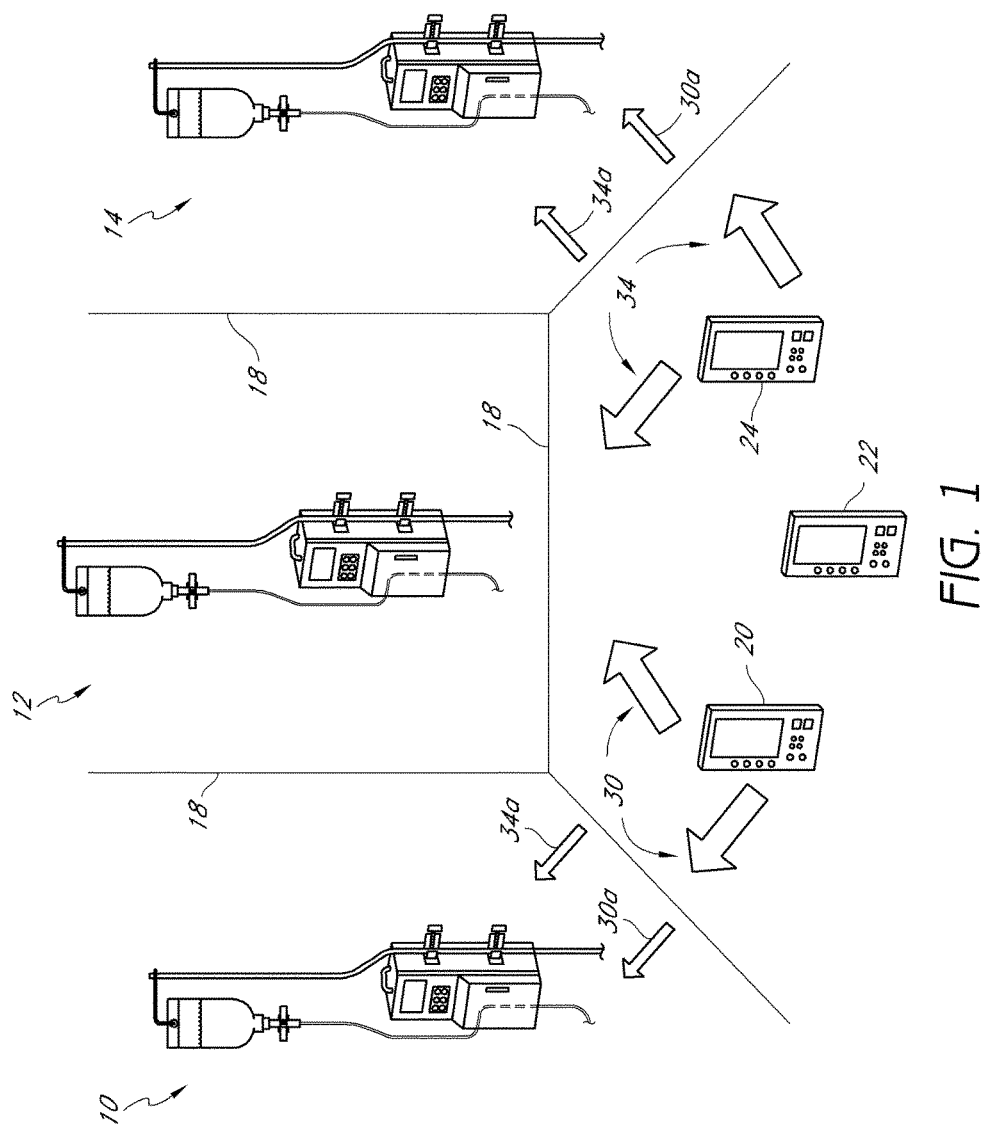
FIG. 1 is a schematic showing multiple infusion devices used in an electromagnetically shielded environment.

U.S. Pat. No. 7,553,295 entitled "Liquid Infusion Apparatus", issued on Jun. 30, 2009, U.S. Pat. No. 7,404,809 entitled "Non-Magnetic Medical Infusion Device", issued on Jul. 29, 2008, and U.S. Pat. No. 7,267,661 entitled "Non-Magnetic Medical Infusion Device," issued on Sep. 11, 2007 are incorporated herein in their entireties by this reference thereto.

The basic characteristics of an infusion pump involve the delivery of medicinal or nutritional liquids, over time, into the venous system of a living subject. IV fluids are pumped at pressures typically in the range of 0.2 to 10 PSI. The infusion device may include detection of over-pressure and have an upper operational limit of about 20 PSI. Flow ranges typical of IV pumps are from 0.1 to 2000 ml/hr. These specifications are different from the specifications for injector devices which are often used in radiologic settings for purposes of rapid bolus injection of image-enhancing contrast agents. Such devices 'push' contrast agents at pressures up to 300 PSI and in very short periods of time in contrast to IV drug delivery systems. Contrast agents are for image enhancement and are commonly delivered using piston or syringe-type pumps that provide the requisite high fluid pressures and rapid deliveries.

The high magnetic field surrounding MRI systems can negatively affect the operation of various devices (including IV control devices), especially those devices that are constructed with magnetic materials, and can seriously jeopardize a patient's safety as a result of devices utilizing magnetic materials that can be attracted at high velocity into the magnetic field where patient or attendant personnel are located.

Devices for infusing liquids into a patient are often attached to an IV pole holding both the infusion device and associated liquids to be infused. Such devices may utilize stepper-type motors or simple DC motors which include magnetic materials for providing the mechanical power required to drive the pumping unit. Further, a control unit receives inputs of prescribed infusion rate settings, and controls the pumping unit to deliver the desired quantity of liquid over time. The control unit may emit spurious radio frequency signals as a result of poor electrical design or insufficient shielding.

Medical devices intended to be used within the MRI environment need special consideration. RF stimulation of atomic nuclei within an associated magnetic field results in the emission of a small RF spin echo from the nucleus so stimulated. In the case of patient imaging, hydrogen nuclei bound with water are the usual targets for magnetic resonance at selected frequencies. Other molecules and compounds can also be selected for study, as in Nuclear Magnetic Spectroscopy, by choosing resonance specific magnetic field strengths and associated radio frequencies. For simplicity the typical hydrogen atom-based image-acquisition process is referred to herein, but it should be recognized that the disclosure is equally useful in spectrographic studies at a plurality of field strengths and frequencies.

Certain devices may be needed in the scan room either to assist with care of the patient being imaged or for the use of attending staff. Of particular interest are those devices placed in the scan room during the time of image acquisition when the patient is present and the magnetic fields are up and RF reception of the tiny nuclear echoes must be cleanly acquired. Electrically passive metallic items such as oxygen bottles or crash carts present safety hazards to the patient due to their potential to be strongly attracted by the magnetic field of the scanner. Such items can be pulled into the imaging volume where the patient is located, creating potential for serious injury or death. Additionally, great effort is made during the manufacture and installation of the scanner/magnet to assure that the lines of flux within the imaging volume are highly homogenous to assure that acquired images have minimal spatial distortion. Thus, devices formed of magnetic material that are positioned within the magnetic field of the scanner can introduce distortions into this homogeneous field and the resultant images. The level of hazard and the degree of field/image distortion due to magnetic materials depends upon the composition and location with respect to the imaging volume.

The hazards due to flying objects can be controlled to some degree by the use of non-ferrous devices such as the aluminum oxygen bottle. Additionally, the gravitational weight of some devices or their rigid fixation in the scanning room may be sufficient to overcome the force of magnetic attraction on the ferrous mass of such devices toward the imaging volume. However, such devices with some ferrous mass, though inhibited from being pulled into the magnetic field, may nevertheless introduce inhomogeneity in the magnetic field. Distortions in the homogeneity of the magnetic field within the imaging volume must be kept at such a level as to be of minimal consequence to the operator reading the resultant image or data. And, the possibility of field distortion is proportionally increased as devices with metallic materials are positioned closer to the imaging volume, with the most critical position being near the center of the imaging volume, essentially where the patient is positioned. Additionally, because of the extremely low levels of RF signals produced by the target image nuclei, great care must be taken to assure that devices with active electronic circuits do not emit spurious RF signals as forms of electronic noise. Such noise can so degrade the signal-to-noise ratio of signals received by the sensor coils and receivers that image resolution is reduced or rendered completely unreadable. Active circuits must be carefully shielded to assure that their RF emissions are extremely low at the specific frequencies of the imaging process. Conversely, it is possible through careful design, to place a source of RF energy for signal transmission, therapy, or the like, within the MRI environment, but such signals should be chosen to avoid the discreet Lamar frequencies unique to the particular magnetic field strength of a given scanner, and should be of such high spectral purity as to coexist without causing any deleterious effects. The intense magnetic fields produced by the scanner can cause detrimental effects on the performance of common DC and stepper motors in devices needed within the scanning room, to the point of making their control difficult or causing their complete failure. The gradient or time-varying magnetic fields can induce changing (AC) currents in motors and associated circuitry which may also cause false motor operation.

An RF shielded room is often used to isolate an MRI system from external sources of electromagnetic fields. The shielded room is designed to significantly attenuate electromagnetic fields under 130 MHz, as most MRI systems operate from 4 MHz to 130 MHz. This shielding may result in the attenuation of other frequency ranges that are not targeted, such as 2.4 GHz signals used for wireless communication. Achieving −100 dB attenuation of targeted signals may inadvertently result in −70 to −80 dB attenuation of signals in the 2.4 GHz range.

It is common to find medical facilities with multiple MR scanners in the same vicinity, often sharing the same control room. It is desirable to provide a remote control for the infusion pump that can be operated, for example, from the control room. More than one infusion pump may be used during a scanning procedure, and it is possible that multiple infusion pumps may be operating at the same time. In one embodiment, allow remote operation of multiple pumps is accomplished by assigning each remote and pump pairing a communication channel.

FIG. 1 illustrates a medical facility with three shielded rooms in the same vicinity. Each room has an infusion pump 10, 12, 14, and is separated from the other rooms and the control room with electromagnetic shielding 18. Each pump has a corresponding remote 20, 22, 24 that is located in the control room. A strong signal 30, 34 is needed to pass through the electromagnetic shielding 18, resulting in an attenuated signal 30a, 34a to communicate with the infusion pump 10, 14. Likewise, a strong signal from the pump is needed to pass through shielding 18 to reach the remote control with minimal signal levels needed for reception. While FIG. 1 illustrates communication from the remote 20, 24 to the pump 10, 14, it is to be understood that there may also be communication from the pump 10, 14 to the remote 20, 24.

The pump's transceiver is located within the pump's shielded housing which keeps internal pump stray RF noise from reaching the MR imaging detector coils and corrupting the images. However, the transceivers antenna should be mounted outside the pump units shielding package. The feed to this antenna should be high pass or band pass filtered so as to allow the 2.4 GHz signals to pass, but not allow image interfering lower frequency RF noise within the scanners frequencies of interest to escape.

In this embodiment, a separate remote for each infusion pump is used. As a result, the control room has three remotes that are broadcasting strong signals. The remotes 20, 22, 24 in the control room may establish a connection with the pumps 10, 12, 14 by transmitting a "hunting" packet. The remotes 20, 22, 24 receive hunting packets from neighboring remotes at full power, which may swamp or overload the receiver circuitry, which makes detection of the weaker signal from the pump very difficult.

In one embodiment, a bi-directional frequency hopping spread spectrum radio link is used for communication between the pump 10, 12, 14 and the remote 20, 22, 24. To alleviate the problems caused by multiple remotes broadcasting strong signals in the same vicinity, a different frequency hopping pattern is used for different connections. Frequency hopping spread spectrum transmissions are spread over a portion of the radio spectrum.

In one embodiment, a 2.4 GHz industrial, scientific and medical (ISM) radio band is used. In one implementation, frequencies are selected in the range from 2.400 GHz to 2.482 GHz. Changing the order of hops through the bands for different connections provides one way of reducing the possibility of multiple devices broadcasting on the same frequency slots in a way that prevents communication.

In one embodiment, the devices may operate utilizing a Bluetooth protocol. The Bluetooth Core Specification version 2.1, available at www.bluetooth.com, is incorporated herein by reference. In one embodiment, the Bluetooth compatible devices may operate in a band stretching from 2.400 GHz to 2.4835 GHz with a lower guard ban of 2 MHz and an upper guard ban of 3.5 MHz. In one embodiment, there may be 79 available channels. In one embodiment, the frequencies of the available channels (in GHz) may be given by the equation $f=2.402+k$ MHz where $k=0, 1, 2 \ldots 78$.

Changing the duration of time a frequency slot is used provides another way of reducing the possibility of multiple devices broadcasting on the same frequency slots in a way that prevents communication. In one embodiment, the duration of use of a frequency slot varies from 8 ms to 18 ms. The duration should be long enough for the radio frequency synthesizer to tune and stabilize at each hop, and then send the packet of data before hopping to the next frequency in the pattern. Using different hop times further reduces the likelihood of two different patterns overlapping.

Figure 2:
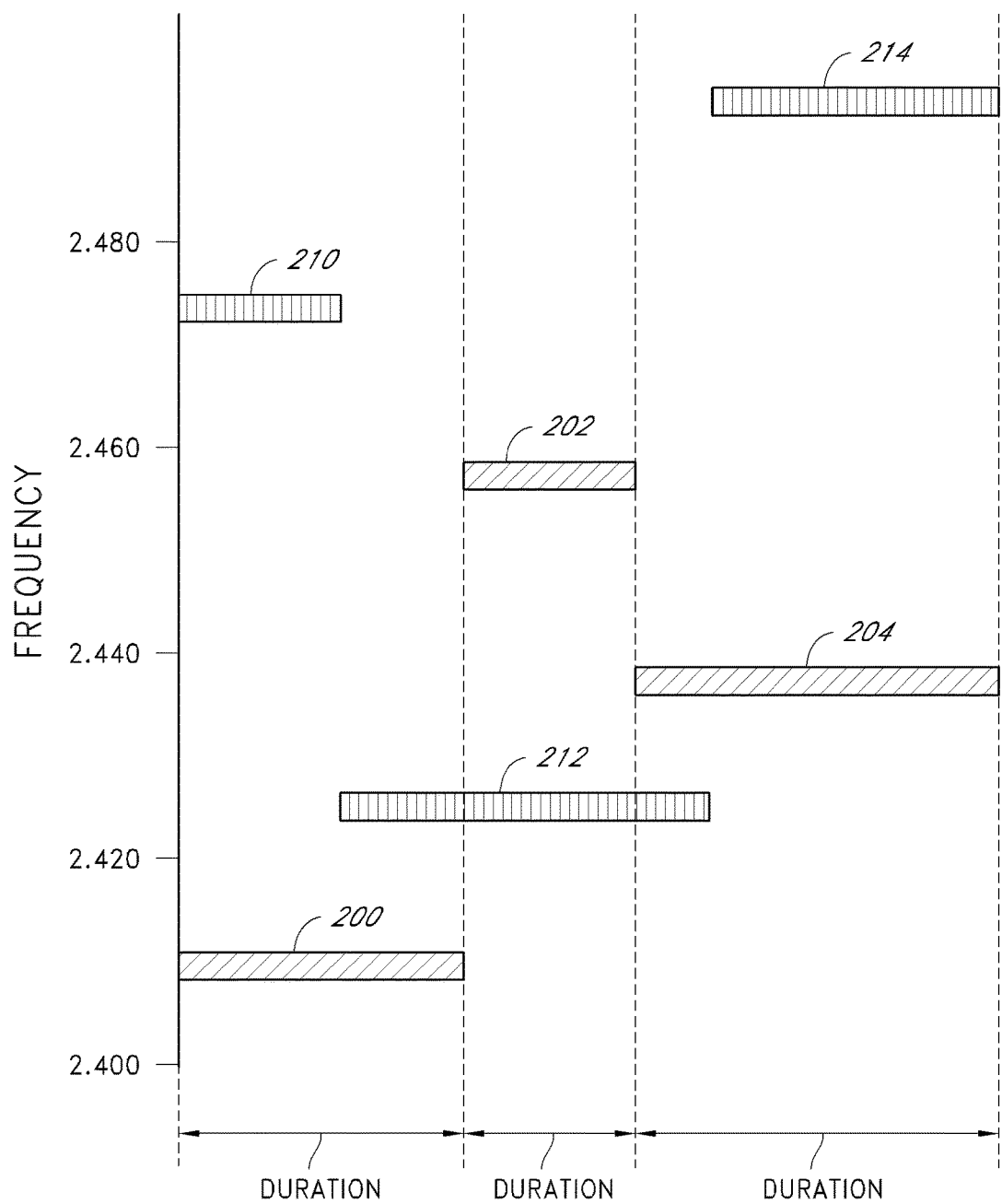
FIG. 2 illustrates exemplary patterns used in a frequency hopping spread spectrum system.

FIG. 2 illustrates an example of using both frequency hopping and changes in duration for a communication link. As illustrated, the frequency can range from 2.400 GHz to 2.480 GHz. Segments 200, 202, 204 represent communication over a first link, and segments 210, 212, 214 represent communication over a second link.

In another embodiment, the hopping pattern can be limited to portions of the available bandwidth. For example, one communication link can be programmed to limit the hopping pattern to the lower end of a band (such as 2.400 GHz to 2.435 GHz) and another communication link can be set to operate at the higher end of a band (such as 2.450 GHz to 2.480 GHz).

It may also be desirable to restrict certain frequencies from being used. For example, if neighboring devices cause interference at particular frequencies, those frequencies can be excluded from the hopping pattern.

In one embodiment, different hopping patterns are presented to a user as channels. The hopping pattern for a particular channel may use different frequency changing patterns, time duration patterns, and/or excluded frequency patterns from another channel.

It should be understood that a remote can communicate with more than one infusion pump. In one embodiment, the remote allows for selection of a channel that coincides with a channel for a specific infusion pump. In another embodiment, the remote cycles through a plurality of channels and provides periodic updates to the remote operator of the status of the infusion pump for one or more active channels.

For each channel, the frequency hopping pattern and time duration pattern could be configured by a user. Alternatively, the patterns could be predetermined. The predetermined patterns could be arranged to avoid conflicts with equipment known to be used in the vicinity or in conjunction with an infusion pump device in various scenarios, such as the MRI environment.

A remote for an infusion pump has application in other areas as well. For example, the remote could be used with a hyperbaric chamber. Hyperbaric chambers provide a pressure greater than sea level atmospheric pressure to an enclosed patient. There are several uses for hyperbaric chambers. For example, the direct pressure in the hyperbaric chamber may be used to treat decompression sickness by slowing the nitrogen release and reducing the size of gas bubbles. Pressurized oxygen may be used to purge carbon monoxide from the body. Vasoconstriction can reduce compartment pressure, edema, swelling, and their consequences. The increased oxygen is bactericidal to anaerobic organisms. In addition, increased oxygen stimulates white blood cells.

The hyperbaric chamber can be used for various purposes, and it is not uncommon to have multiple individuals in the same hyperbaric chamber. Once the chamber has been pressurized, it is inconvenient to interrupt the session, especially if multiple patients are in the chamber. Some patients in the chamber may be connected to a liquid infusion device, which may need to be adjusted during the session. Allowing the liquid infusion device to be controlled remotely alleviates the need to interrupt a session if the settings need to be changed.

Figure 3:
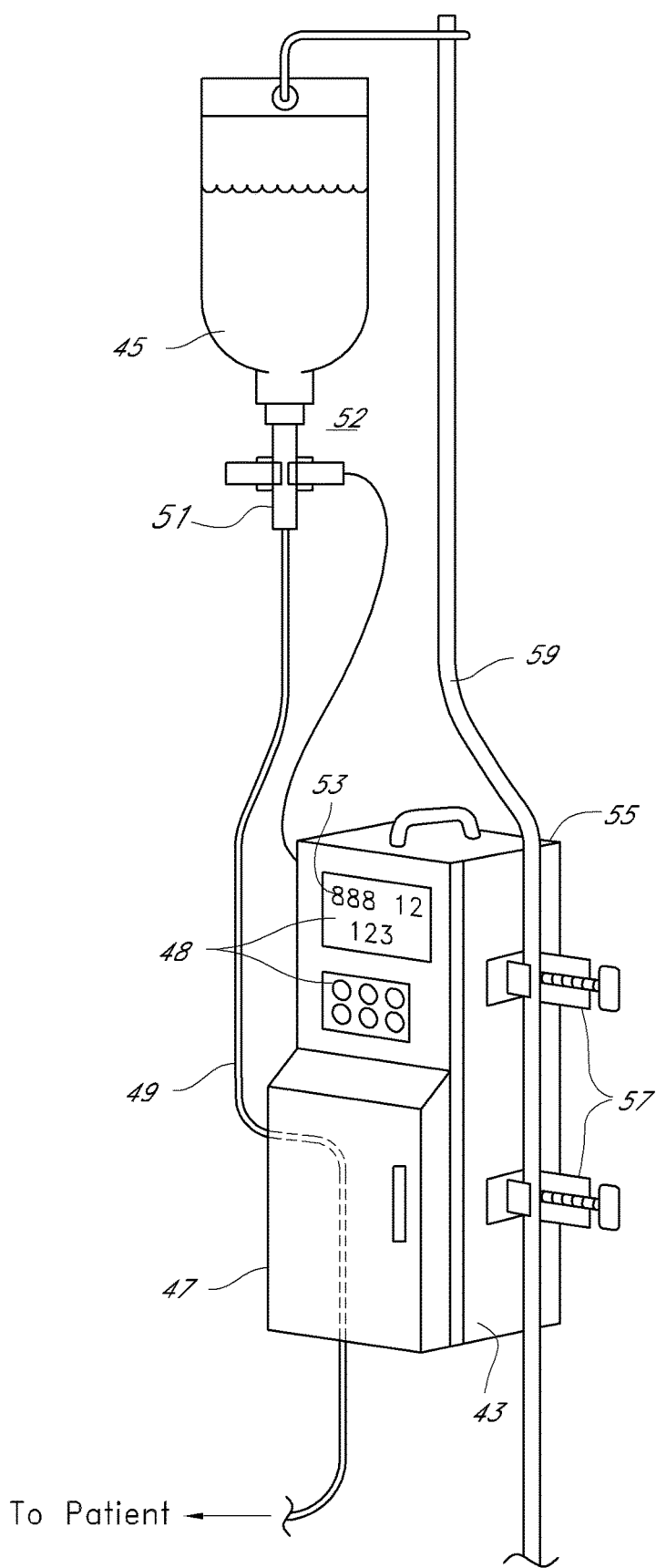
FIG. 3 is a partial perspective view of an infusion device in accordance with one embodiment.

FIG. 3 illustrates one embodiment of a liquid infusion device 43 that is operable within an electromagnetically shielded room or a hyperbaric chamber. The liquid infusion device 43 is also operable within intense magnetic fields and with negligible RFI to provide positive displacement of a liquid 45 such as saline or antibiotics, or sedative, or the like, in controlled volumes per unit time. The device does not include any ferrous or magnetic materials, and is substantially shielded against irradiating any RFI during operation. The device 43 includes a pump in the lower chamber 47 that receives therein a flexible, resilient tubing 49 that is prepackaged and sterilized as a component of an IV liquid infusion set. Drip chamber 51 is also part of the infusion set. Controls for the pump in chamber 47 include an operator's input keypad 48 that is shielded against radiation of RFI for setting infusion parameters, and a drip detector 52 that may be disposed about the drip chamber 51 to detect flow of liquid from the supply 45. A display 53 is positioned in the housing 55 which may be formed of non-magnetic, RF-shielding material such as conductively-coated plastic or aluminum, or the like. The housing 55 attaches with, for example, clamps 57 to a rigid support 59 formed of non-magnetic material such as fiberglass or aluminum, or the like.

FIG. 4 illustrates a pump 406 and a corresponding remote control 408. In this embodiment, the remote utilizes controls that mirror the controls located on the pump. For example, the remote controls may include the start or stop of fluid flow, silence of alarms, or setting or titrating a fluid delivery rate or volume. An alarm condition for the pump 406 would also be indicated by the remote control 408. An infusion device may have dual pumps which can be controlled independently. In one embodiment, a side car module is attached to the pump to provide a second channel for infusion delivery. Each of the pumps may be fully controlled by the remote control 408. It should be understood that the controls on the remote are not necessarily coextensive with the controls on the pump.

In one embodiment, the display on the remote may also mirror the display located on the pump. For example, the remote may display alarm conditions or the status of the battery at the pump. Again, the information displayed on the remote is not necessarily coextensive with the information displayed on the pump.

In one embodiment, the remote acts as a charger for a spare pump battery. The charge status of the spare battery may be displayed by the remote.

One pump could be used to remotely control other pumps. For example, a pump could be placed in the control room, and that pump would then communicate with pumps being used with a patient. In another embodiment, a pump that is being used with a patient could also be used to remotely communicate with a pump being used with a different patient. Accordingly, "remote" as used herein may refer to a device that is not physically attached to a pump, although in some embodiments a remote may be part of one pump that is used to control another pump.

In one embodiment, controls at the remote and the pump may be operated simultaneously. For example, an operator in the control room and another operator near the patient may both adjust operation of the pump through controls that are local to each operator. Changes in the display would be communicated to both the operator in the control room and the operator near the patient, so that both operators can see the effect of the others actions.

In one embodiment, the pump operates without the remote or if communication between the remote and the pump is interrupted. Displays on the pump and remote may indicate the connection status and relative signal level. The remote may provide an alarm if the connection is interrupted.

In one embodiment, the remote uses selectable communication channels. For example, a remote may be used to communicate with more than one pump. Similarly, multiple remote/pump pairings may be used in the same vicinity.

Figure 5:
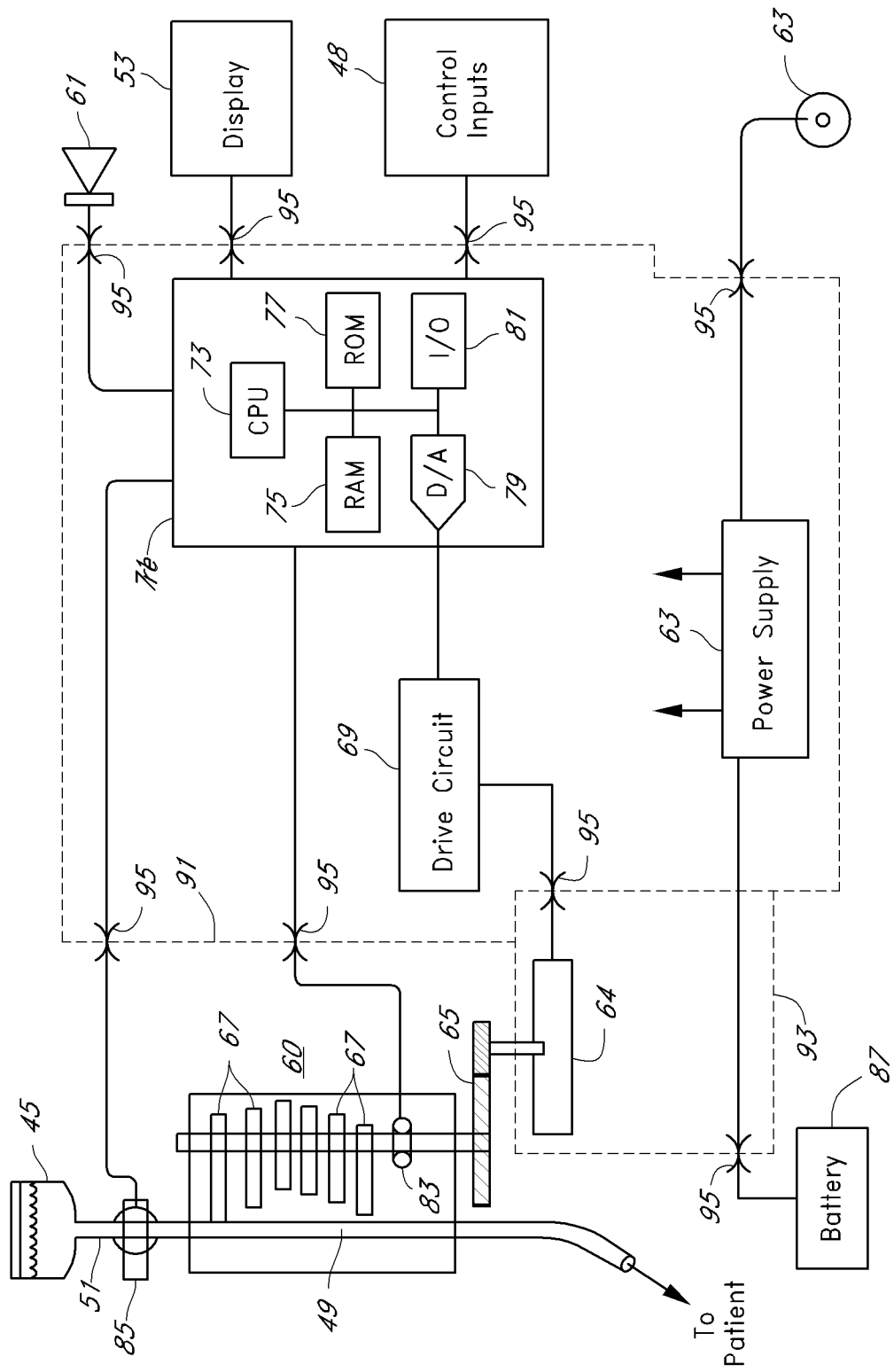
FIG. 5 is a block schematic diagram of the infusion device of FIG. 3.

Referring now to the pictorial block schematic diagram of FIG. 5, there is shown a peristaltic-type positive-displacement pump 60 disposed within the pump chamber 47 of the housing 55 to operate with the length of tubing 49 that passes therethrough between the drip chamber 51 and the patient. The peristaltic pump 60 (linear or rotational) is driven by an ultrasonic motor 64 via appropriate mechanical linkage 65 to actuate a squeeze roller against the tubing 49, or to actuate a series of elements 67 through a linear tubing-squeezing sequence to produce peristaltic pumping action. Various visual and audible annunciators 61 may be provided to signal operational conditions either within acceptable limits, or within error or failure conditions.

An ultrasonic driving motor 64 is powered by multiphasic signals applied thereto from the motor drive circuit 69. A controller 71 for the device includes a central processing unit 73 with associated peripheral components including Random Access Memory (RAM) 75, Read-Only Memory (ROM) 77, Digital-to-Analog (D/A) converter 79, and an Input/Output channel 81. This controller 71 receives input control information from the operator's keypad 48, and receives feedback information about pump speed and position from sensor 83 and about liquid flow from drip detector 85 disposed about the drip chamber 51. In response to the inputs supplied thereto, the controller 71 operates on stored programs to actuate a display 53 of operating parameters (or other data), and to actuate the motor drive circuit 69 for energizing the ultrasonic motor 64 for rotation at a controlled speed. A power supply 63 is connected to the controller 71 and drive circuit 69 to supply electrical power thereto, and is connected to a battery 87 to receive electrical power therefrom during stand-alone operation, or to receive line voltage via plug 63, as required.

In accordance with one embodiment, no magnetic material is used in any of the components of the infusion device 43 including the ultrasonic motor 64, pump 60, power supply 63, controller 71 and associated components. Additionally, none of such components is adversely affected during operation by a strong magnetic field. And, any RF energy that may be generated by electronic signals within the ultrasonic motor 64, drive circuit 69, controller 71, power supply 63 or associated components is specifically shielded by conductive structures 91, 93 disposed around such components to inhibit radiation of RFI. Additionally, radio-frequency interference filters 95 are disposed about all through-shield conductors to inhibit radiation of RFI through such portals.

Referring now to FIG. 6, aspects of the liquid-delivery systems in accordance with one embodiment is shown. A liquid conduit 404 includes a fluid connector 402 at an input or proximal end, and includes a flanged connector 701 that couples the proximal segment of the liquid conduit 404 to an intermediate segment including a length of precision tubing 703 that terminates in flow valve 705. The assembly is prepared and sterilized and packaged in an hermetically-sealed envelope for installation in a pumping device 406, as needed to infuse liquid into a patient.

The precision tubing 703 may be formed as a thin-walled extrusion of a flexible, elastic material such as silicone rubber, or other biocompatible polymer that confines a selected liquid volume per unit length within the bore of selected cross-sectional dimension between the flanged connector 701 and the flow valve 705. In this way, progressive peristaltic pumping by successive pinching and advancing of the pinch point along the tubing 703 toward the flow valve 705 administers a known volume of liquid to a patient. The length of tubing 703 between flanged coupling 701 and flow valve 705 may be slightly stretched into position within the pumping device to provide resilient engagement of the flanged connector 701 and flow valve 705 within their respective mating receptacles 706, 708 disposed at opposite ends of the active peristaltic pumping mechanism of the pumping device.

Figure 7:
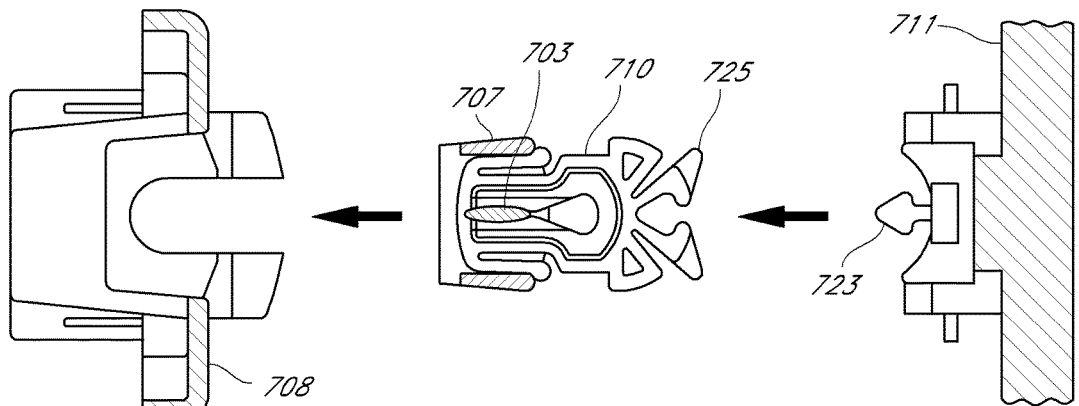
FIG. 7 is an exploded top view of valve apparatus.

The flow valve 705, as illustrated in the exploded top view of FIG. 7, includes an outer housing 707 within which the precision tubing 703 passes. The mating receptacle 708 in the pumping device for the housing 707 includes a complementary recess that receives the housing 707 in only one orientation and secures the properly-installed housing in place with the aid of slight tension exerted thereon by tubing 703. A slide or shuttle element 710 is disposed within the housing 707 to slide laterally relative to the elongated axis of the tubing 703, with the tubing 703 passing through a tapered aperture in the shuttle element 710. Thus, with the shuttle element 710 fully depressed within the housing 707, the tubing 703 passes through the portion of the aperture of maximum cross sectional dimension, leaving the bore of the tubing 703 fully open for unimpeded flow of liquid therethrough. In alternate position of the shuttle element 710 maximally protruding from the housing 707, the tubing 703 is pinched within a portion of minimal cross-sectional dimension of the aperture, as shown, to inhibit liquid flow through the tubing 703. Thus, as initially installed within the pumping device, the flow valve 705 is configured to inhibit flow through the liquid conduit 404 to ensure no inadvertent dosing of a patient until the pumping device is rendered operational.

In accordance with one embodiment, the pumping device is inhibited from administering liquid to a patient until a liquid conduit 404 is properly installed and an access door 407 is fully closed and safely latched shut. The access door 407 carries passive components of interlocking elements that properly engage and interface with active components of the device 406 for proper operation only with the access door 407 fully closed and safely latched shut. The region of the device 406 that is accessed through the opened access door 407 includes a generally vertical channel for receiving the flanged connector 701 in a complementary receptacle 706 that is positioned above the peristaltic pumping mechanism 712. A sensor may be disposed above the receptacle for the flanged connector to optically sense presence of liquid in the proximal portion of the conduit 404, and operate to inhibit the pumping device 406 from further pumping activity in response to sensing an empty conduit.

Figure 10:
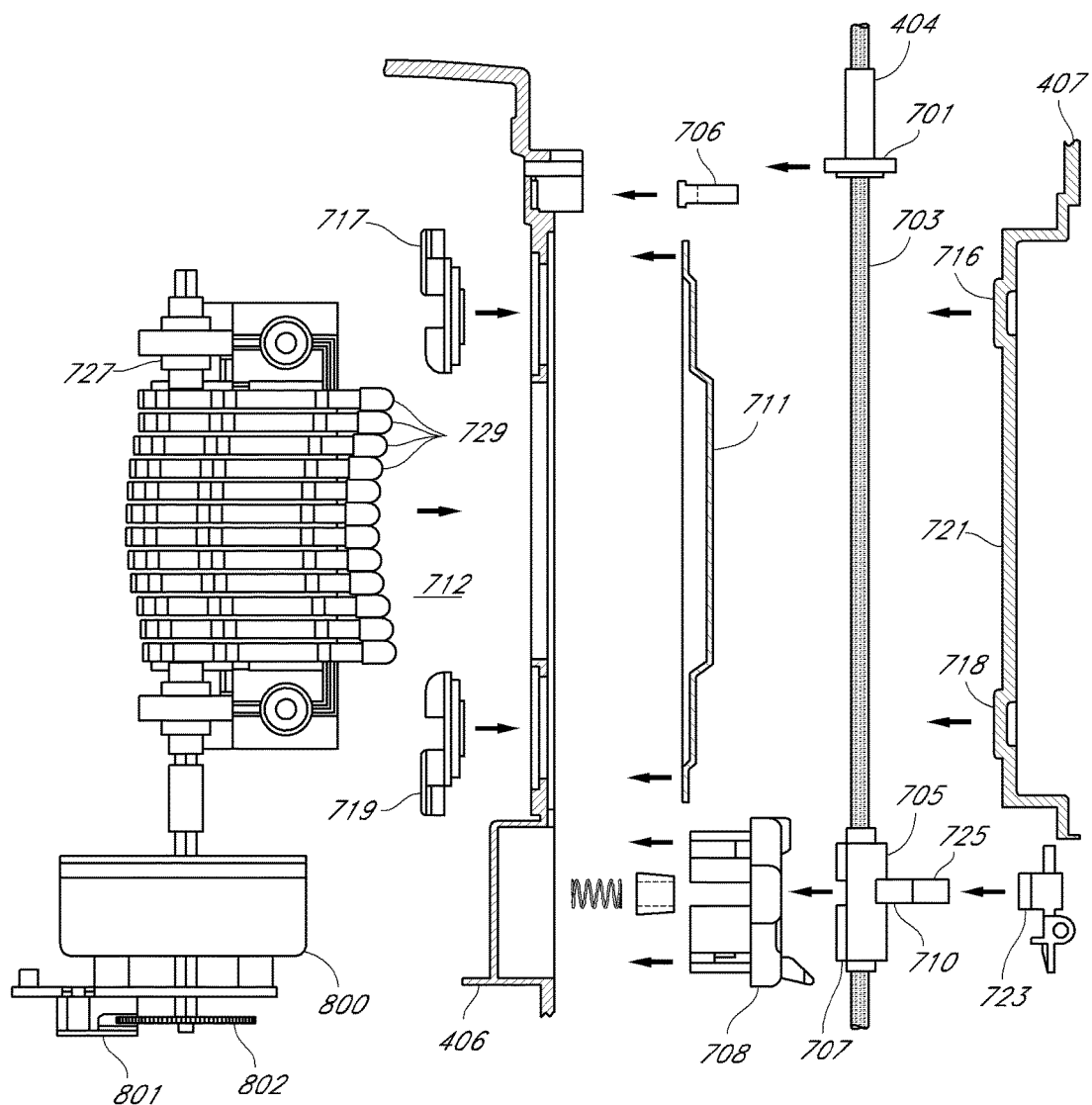
FIG. 10 is an exploded side view of operative components.
Figure 11:
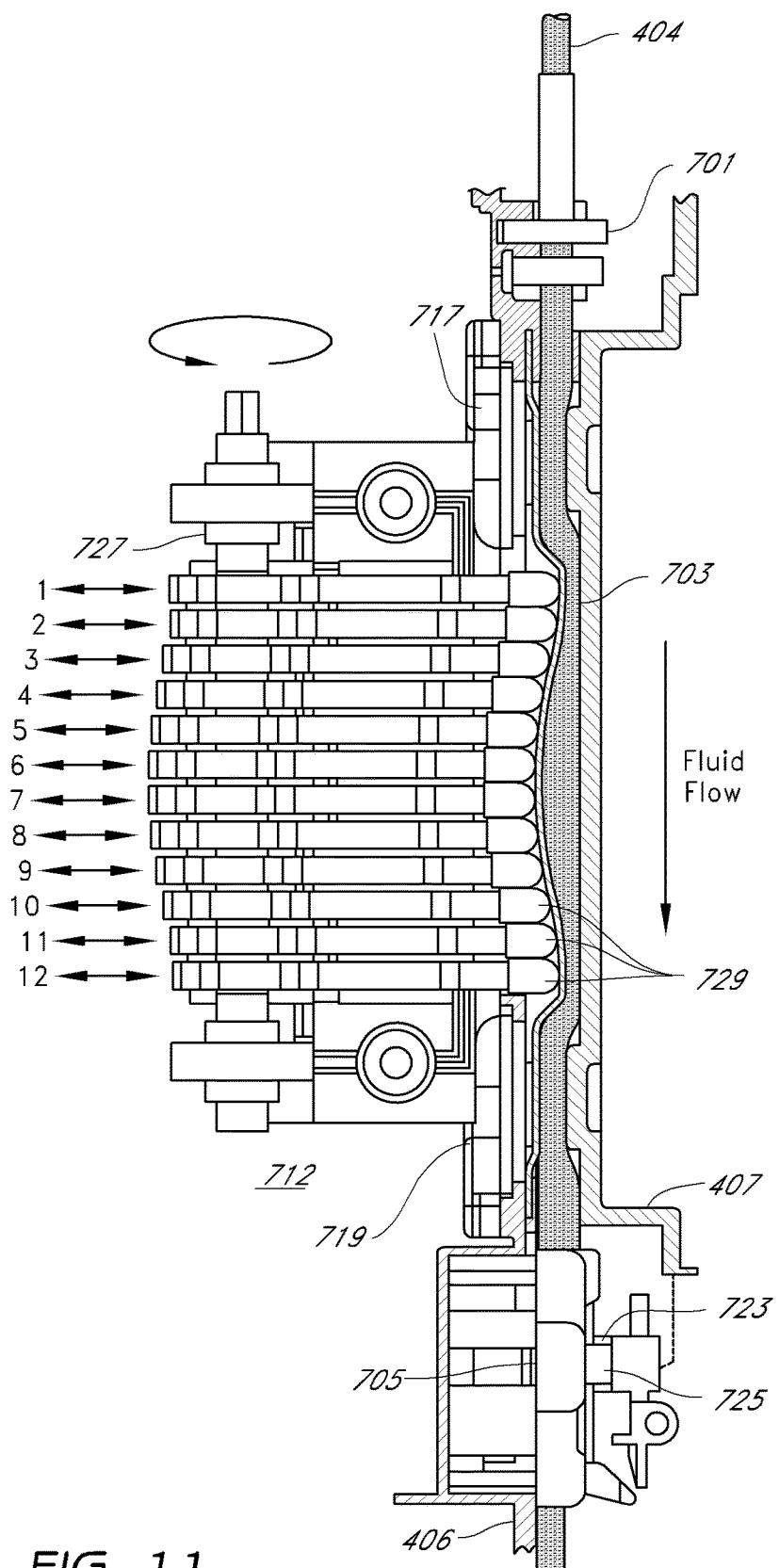
FIG. 11 is a partial side view of the embodiment of FIG. 10 in assembled, operational configuration.

As illustrated in FIGS. 10 and 11, the access door 407 carries an upper platen 716 that cooperates with a pressure sensor 717 disposed behind a flexible membrane 711 and intermediate the receptacle 706 for the flanged connector 701 and the peristaltic pumping mechanism 712 to position an initial length of installed tubing 703 between spaced platen 716 and pressure sensor 717. In this way, the pressure at which liquid is supplied to the device can be tonometrically determined within the precision tubing 703, or otherwise measured, for use in correcting calculation of pumping activity required to deliver a selected volumetric infusion rate of liquid to a patient.

Similarly, a platen 718 is carried on the access door 407 at a location aligned with another pressure sensor 719 disposed intermediate the pumping mechanism 712 and the flow valve 705. In the manner, similar to operation of pressure sensor 717, the pressure sensor 719 and platen 718 confine the precision tubing 703 to provide tonometric measurement, or other measurement, of outlet pressure. An upper limit of outlet pressure may be selected to trigger an alarm condition if such liquid outlet pressure exceeds the set limit as an indication of a clogged outlet conduit.

The access door 407 also carries a platen 721 positioned in alignment with the peristaltic pumping mechanism 712 to confine the precision tubing 703 therebetween to effect linear peristaltic pumping activity in the generally downward direction from inlet pressure sensor 717 toward outlet pressure sensor 719. Neither pressure sensing nor pumping activity may proceed until the access door 407 is fully closed to position the associated platens about the precision tubing 703 for proper sensing and pumping operations.

Figure 8:
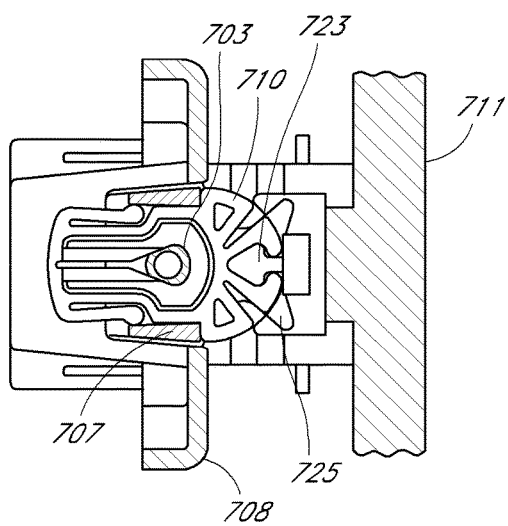
FIG. 8 is a top view of the valve apparatus of FIG. 7 in one operating configuration.
Figure 9:
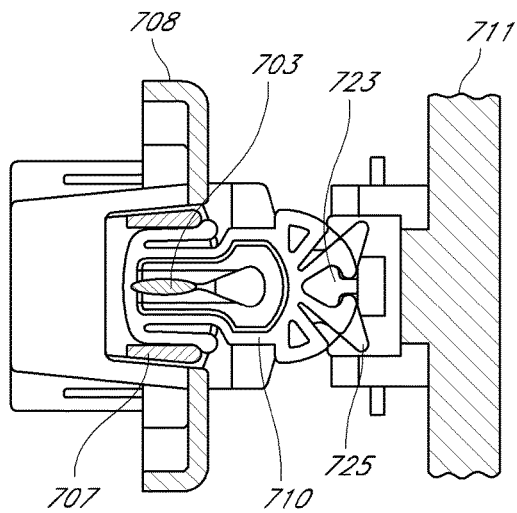
FIG. 9 is a top view of the valve apparatus of FIG. 7 in another operating configuration.

The access door 407 also carries a detent element 723 that mates with a resilient clamp 725 carried on the shuttle element 710 of flow valve 705. Specifically, these mating elements effect sliding movement of the shuttle element 710 from initially protruding position (i.e., tubing 703 pinched) toward fully open position (i.e., tubing 703 not pinched) as the access door is closed, as illustrated in FIG. 8. Additionally, the engaged detent element 723 and resilient clamp 725 remain engaged as the access door 407 is initially opened, thereby to pull the shuttle element 710 toward maximum protrusion from the housing 707 to pinch tubing 703 and inhibit further liquid flow therethrough, as illustrated in FIG. 9. The attachment of the resilient clamp 725 carried on the shuttle element 710 of flow valve 705, and the detent element 723 carried on the access door 407 is overridden and resiliently released following maximum protrusion of the shuttle element 710 and further opening of the access door 407. Of course, detent element 723 may be carried on the shuttle element 710, and a resilient clamp 725 may be carried on the access door 407 to effect similar interaction and safety operation.

Referring to FIG. 10, an ultrasonic or optical sensor may be disposed within the device 406 at a location thereon below the flow valve 705 and about the distal segment of the liquid conduit 404 to detect the presence of air bubbles in an outlet conduit that is formed of ultrasonically or optically-transmissive material. This sensor may include a protruding U-shaped receptacle for receiving the conduit therein and for supporting optical elements in the protruding arms of the receptable to sense bubbles in liquid passing therebetween in the outlet flow of liquid within the conduit. A mating U-shaped element is supported on the access door in alignment with the U-shaped receptacle of the bubble detector to capture the liquid conduit 404 fully recessed therein in order to fully close the access door 407.

Referring to the partial side view of FIG. 11, there is shown a partial side view of the components of FIG. 10 assembled into operational configuration. Specifically, the access door 407 disposed in closed configuration positions the platens 716, 718, 721 on one side of the intermediate length of precision tubing 703 against the respective sensors 717, 719 and pumping mechanism 712. The flow valve 705 is configured to open condition and liquid is pumped through the conduit 404, 703 in response to rotation of the cam shaft 727 of the peristaltic pumping device 712. In this manner, pinch points along the precision tubing 703 progress downwardly as successive pump elements 729 of the pumping device 712 are manipulated by the rotating cam shaft 727 to provide the peristaltic pumping action.

Figure 12A:
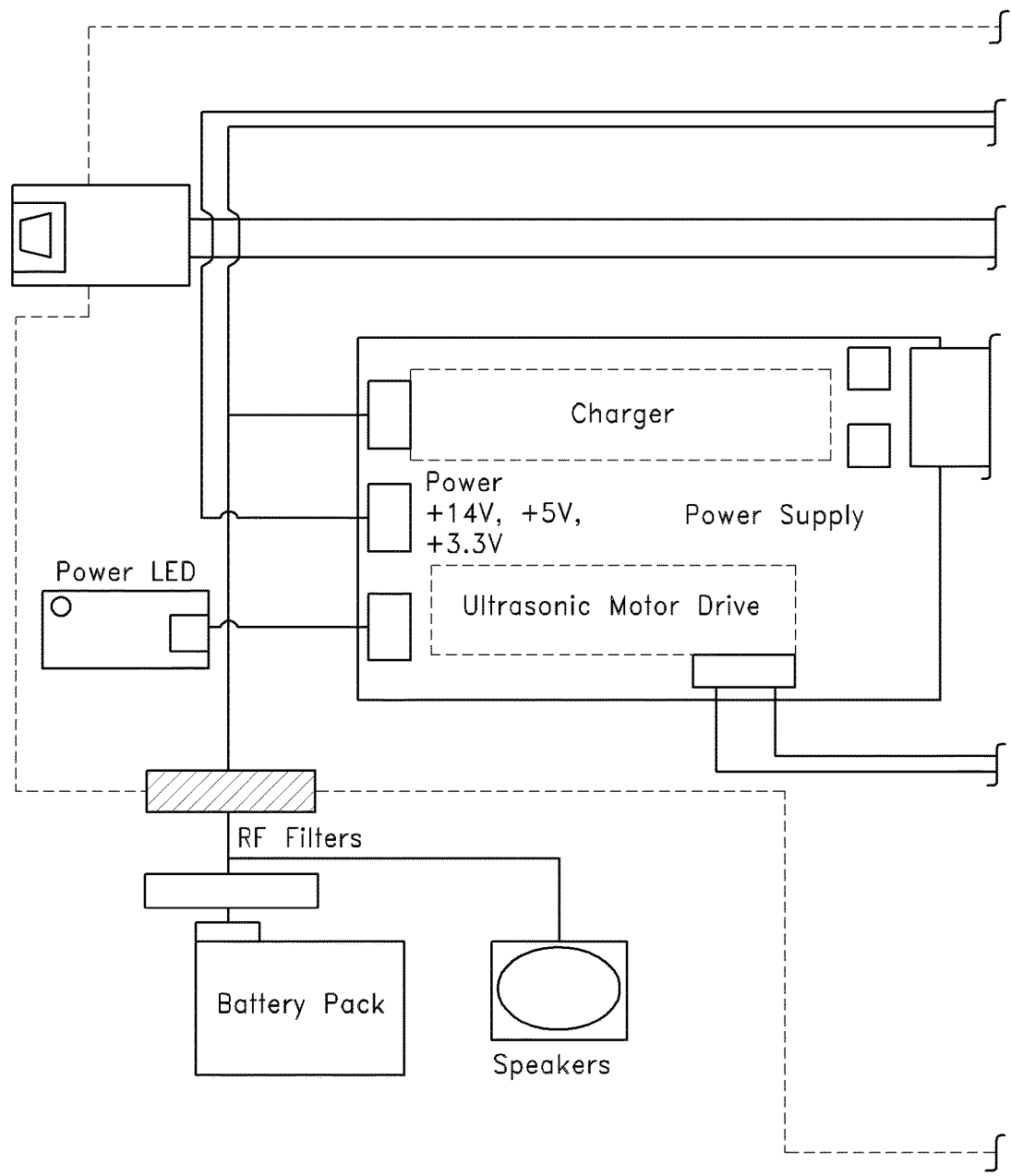
FIGS. 12A-12C depict a block schematic diagram illustrating operating components.
Figure 12B:
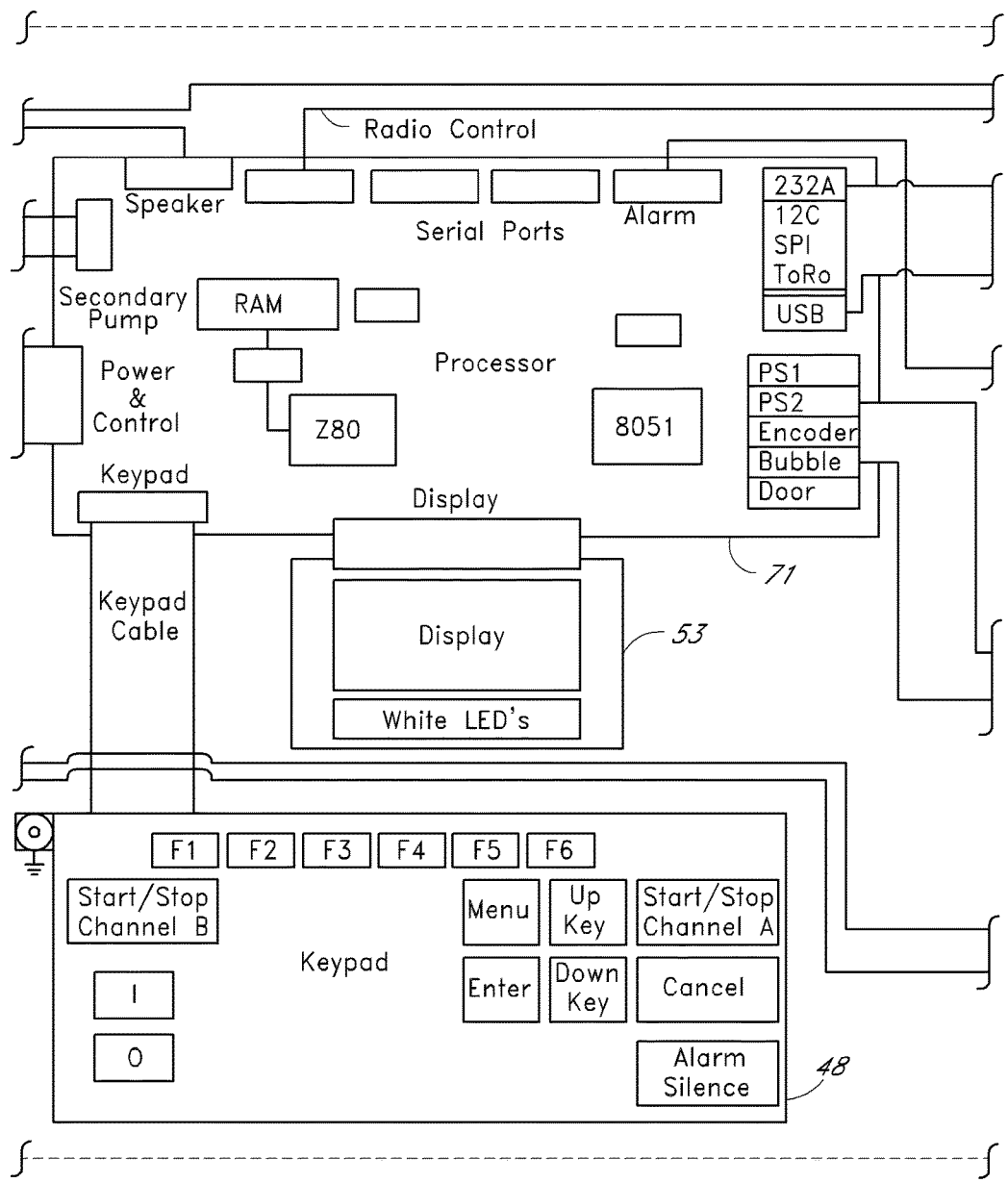
Figure 12C:
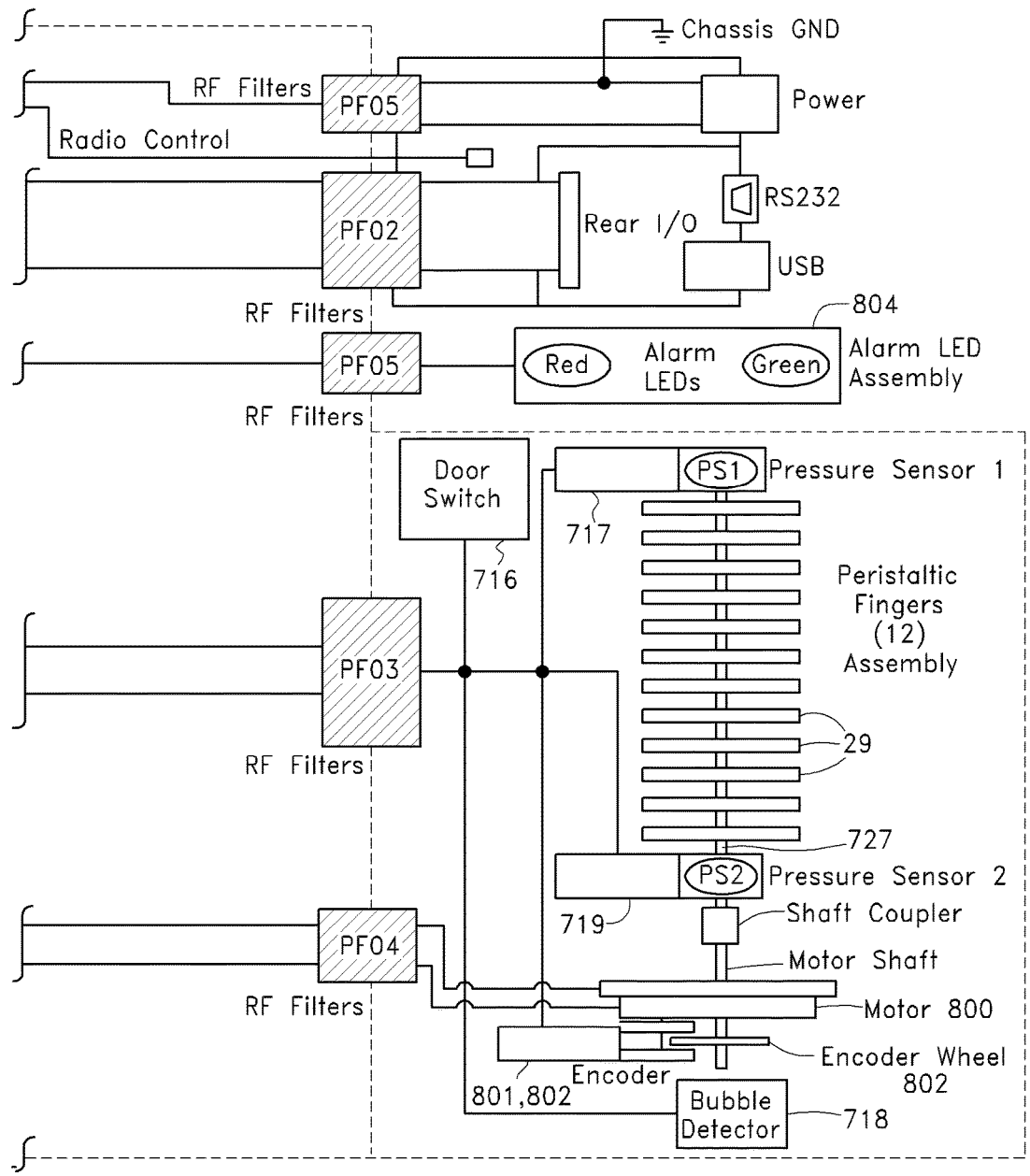

Referring now to FIGS. 12A-12C, there is shown a block schematic diagram of the operational components of the fluid delivery system according to one embodiment. The peristaltic pump includes pumping elements or fingers 729 that are manipulated in a pumping sequence in response to rotation of the shaft 727. The output shaft of ultrasonic motor 800 is coupled to the pump shaft 727 that carries an optical encoder disk 802. Optical sensing elements 801, 802 detect peripheral marks and an index mark for producing outputs indicative of disk position and speed of rotation. In one embodiment, a light source transmits light through the peripheral marks to optical sensing element 801, and the light source also transmits light through the index mark to optical sensing element 802. In one embodiment, the peripheral marks are spaced to generate 1,000 optical pulses per revolution. In one embodiment, the index mark generates one optical pulse per revolution. In another embodiment, a plurality of index marks may be configured in, for example, a gray code pattern. In a further embodiment, a single sensor is used to detect both the peripheral marks and the index mark, where the index mark may be distinguished, for example, by creating a longer optical pulse. These outputs are supplied to the controller 71 that also receives control signals from manual-entry keyboard 48 and from pressure sensors 717, 719, bubble detector 718 and access door safety switch 716. The controller 71 generates multiphasic drive signals via drive circuit 69 and, among other functions, controls the display 53, alarm indicators, and the like.

Figure 13A:
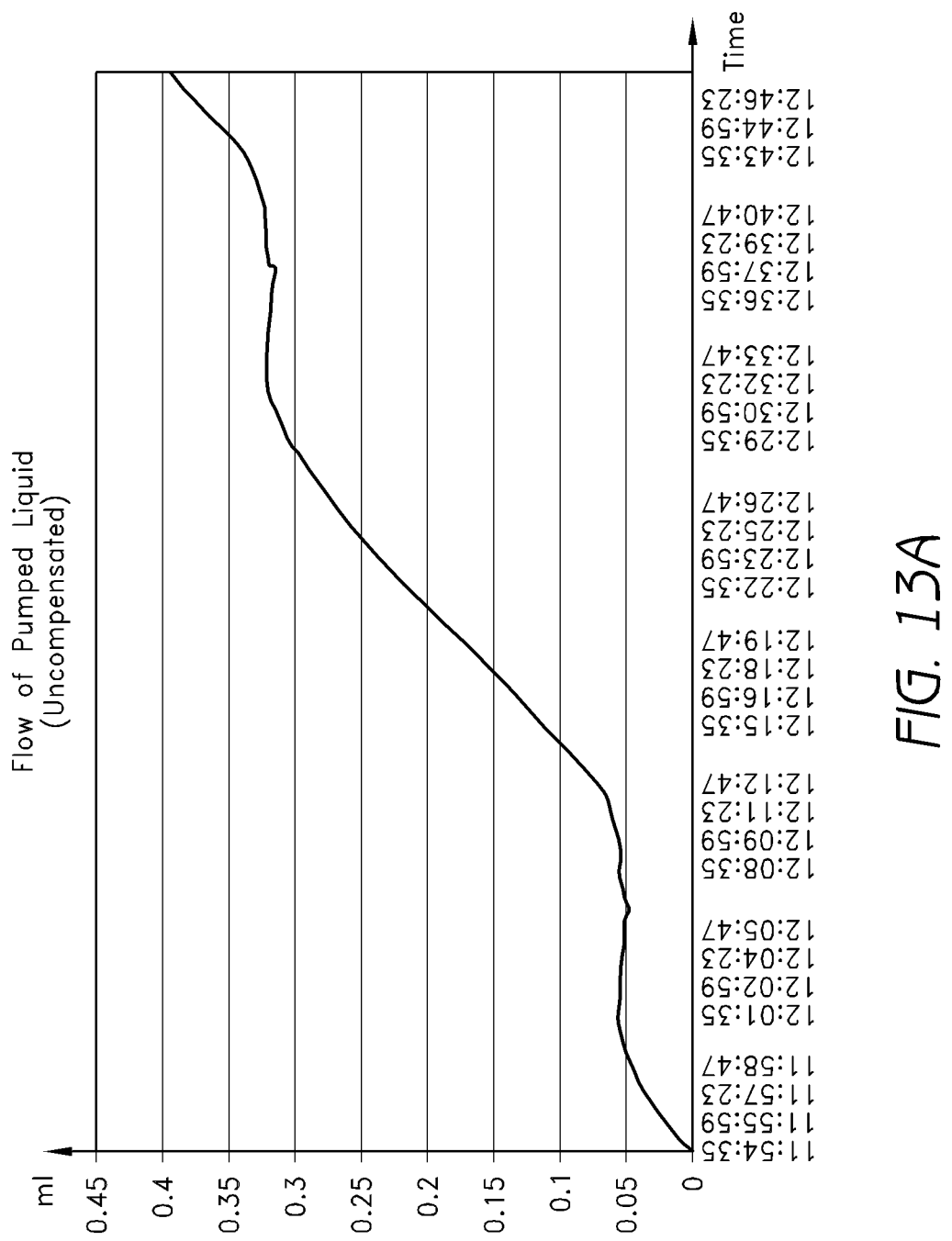
FIG. 13A is a chart illustrating typical flow rate through a linear peristaltic pump operating at constant speed.

The linear peristaltic pump mechanism may provide a high degree of control in order to assure accuracy and linearity of fluid flow rate. The operating speed of the pump shaft is modulated to overcome flow-rate non-linearities or discontinuities commonly experienced within a peristaltic pumping cycle, as illustrated in the chart of FIG. 13A, of fluid flow rate over time at constant shaft speed. For this reason, the controller 71 uses signal information indicative of the location of pump elements during the interval of a pumping cycle in order to determine requisite speed modulation and when to apply the speed modulation during a pumping cycle. FIG. 13A shows the uncompensated flow output of the peristaltic pump according to one embodiment operating at a very slow RPM rate, over slightly more than one revolution (one cycle of 12 pump fingers) that takes about 31 minutes and delivers about 0.32 ml of fluid. It should be noted that there exists a no-flow "dead band" of approximately 11 minutes in the 31 minute cycle, including a small discontinuity. The discontinuity is dependent on very small mechanical tolerances such as the lengths of the fingers, the perpendicularity of the platen to the fingers, and the likes which vary pump to pump. However, the long 11-minute dead band is very similar pump to pump.

Fine control of pump-flow characteristics is established utilizing modulation of the rotational speed during each cycle of the peristaltic mechanism. The resultant flow, as illustrated in the graph of FIG. 13B resembles the smoothness and linearity of syringe-fine pumps, a desirable characteristic when infusing potent drugs or infusing small patients, i.e., babies.

Figure 13B:
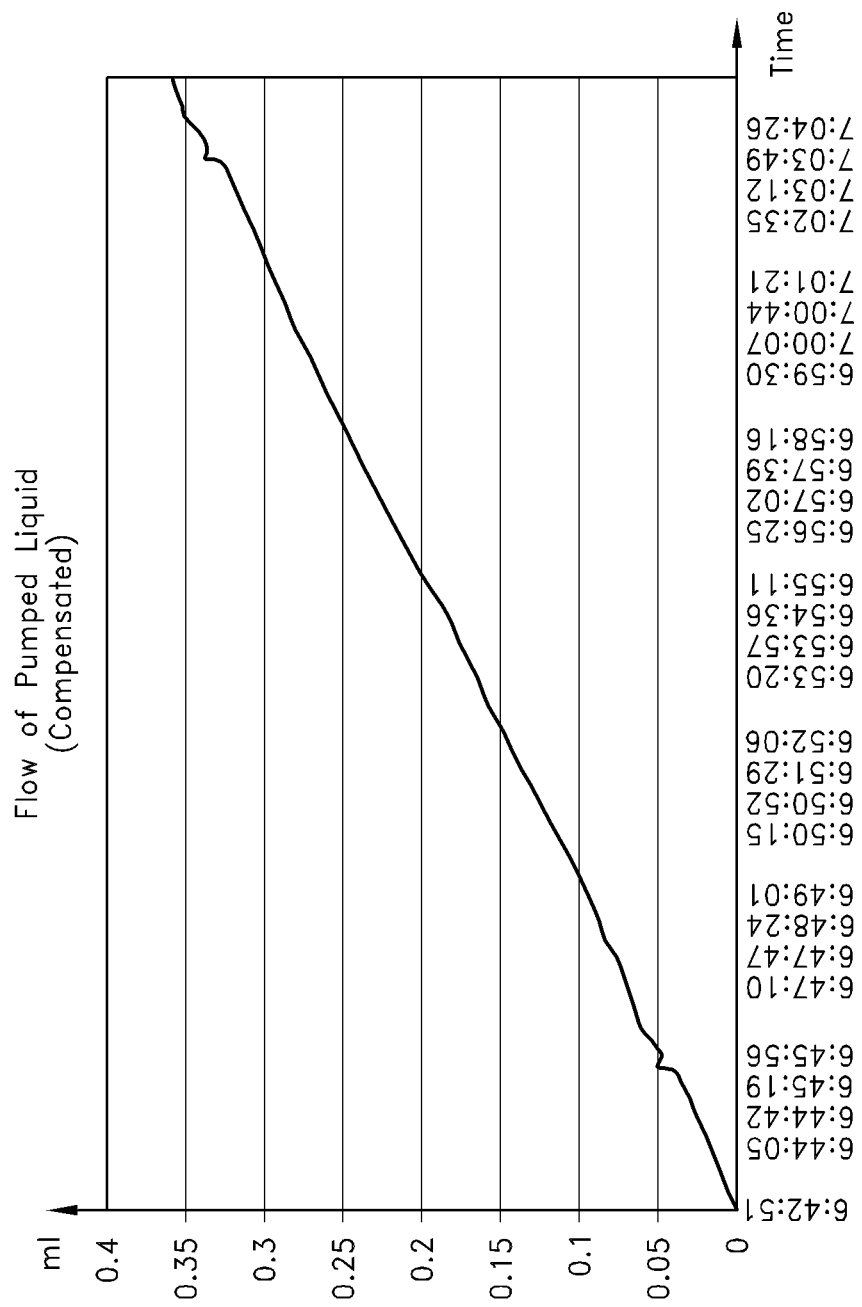
FIG. 13B is a chart illustrating flow rate through a linear peristaltic pump operating in compensated manner.

Specifically, FIG. 13B shows the flow output of the pump resulting from speed 'modulation' applied to each rotation. The rotational speed modulation is accomplished using, for example, 8 discrete different speeds of the motor and pump during the dead band interval. To accomplish such speed modulation for flow correction, the drive motor 800 should be able to start and stop very quickly and in very small angular displacement typically in the range from about 3 to about 10 milliseconds, and within about 0.3 to about 0.9 degrees of arc. The encoder 801, 802 outputs of index and 1000 pulses per revolution indicate to the controller 71 the starting position of the dead band (index plus mechanical offset by number of pulses counted) for compensation and the exact (i.e., the rotational distance as pulses counted) to control timing and application of the discrete speeds. After compensation is applied in this way, the flow output of the linear peristaltic pump is very linear in delivering very precise amounts of fluid of about 1 ml/Hr. The lowest pump rate (1 ml/HR) is a basis for compensation as at high speeds the dead band is inherently shorter and less consequential.

The optical encoder 801, 802 provides both fine and coarse output indications of the disk position and speed of rotation. Specifically, one index mark is sensed to identify the exact angular position of the pump shaft 727, and numerous peripheral graticule marks (e.g., 1000 about the periphery) provide fine indication of angular re-positioning of the shaft relative to the index mark. Of course, the frequency of recurrence of sensed graticule marks also indicates rotational or angular speed of shaft 727. Thus, the controller 71 receives control signals from the optical encoder 801, 802 that facilitate modulation of motor speed in the manner as described above to overcome discontinuities or anomalies in a selected flow rate of fluid through the peristaltic pump as illustrated in FIG. 13B, during portions of the pump cycle driven by the ultrasonic motor 800.

In order to accomplish fine resolution of fluid flow rates through the peristaltic pump, the drive motor 800 should be able to start and stop very rapidly, typically within the range of about 3 to 10 milliseconds. Quick starting and stopping is used with control signals from the processor which pulse drive the motor and therefore make it move in very short steps. It is this ability to pulse drive the motor in short bursts of movement that allows modulation of the speed down to very slow levels when low fluid flows are desired.

Figure 14:
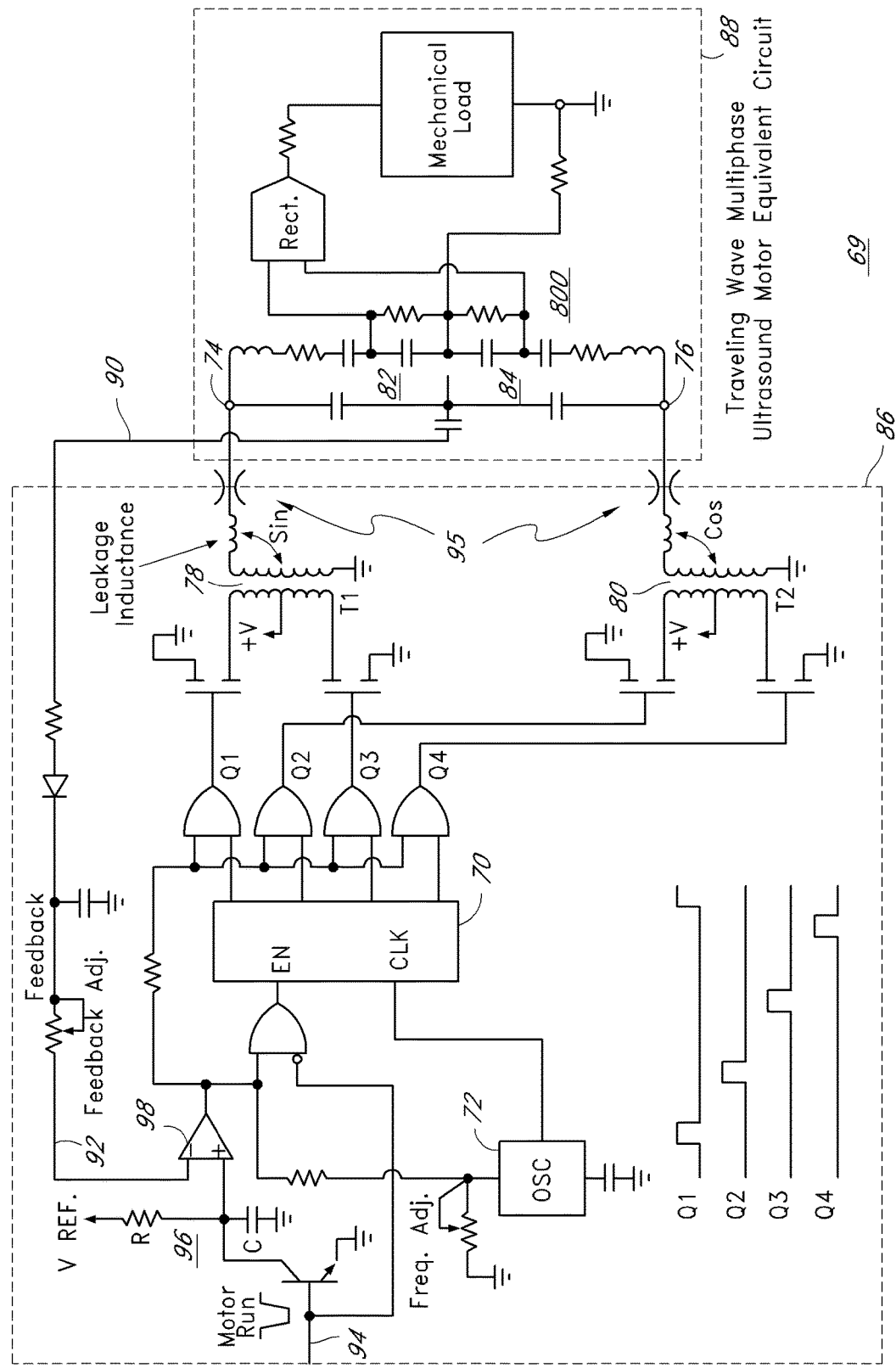
FIG. 14 is a schematic diagram of drive circuitry for a multiphasic ultrasonic motor.

The driving ultrasonic signals are generated by the drive circuit 69 at about 43 KHz with very low harmonic content in the range of about 6 or 8 MHz to about 130 MHz within which MR scanners are sensitive to RF signals. This is accomplished on the drive circuit 69, as shown in the schematic diagram of FIG. 14, using a shift-register type of counter 70 that receives input from voltage-controlled oscillator 72 to generate high-voltage ultrasonic frequencies in sine and cosine relationship 74, 76. Coreless or air core transformers 78, 80 are driven push-pull through field-effect power transistors that receive paired outputs from the register 70. The primary inductance (through the turns ratio) and the leakage inductance of these transformers 78, 80 coact with the characteristic input capacitance 82, 84 of the ultrasonic motor 800 to produce substantially sinusoidal, high-voltage drive signals 74, 76 of low harmonic content. These sinusoidal drive signals also pass efficiently through the filters 95 from the electrically shielded controller section 86 to the electrically shielded motor section 88, and exhibit concomitant low to negligible RF interference attributable to drive signal harmonics.

It should be noted that the ultrasonic motor 800 provides an AC signal 90 representative of the composite sine and cosine drive signals. This AC signal 90 is rectified and integrated or low-pass filtered to produce a DC voltage level 92 that is indicative of motor speed, and is distinguishable from the position and rotational speed indications digitally derived from the optical encoder 801, 802. The analog DC voltage level 92 is applied via the operational amplifier 98 to the voltage-controlled oscillator 72 in order to control the frequency of the motor drive signals. Specifically, the rotational speed of the ultrasonic motor 800 varies inversely with frequency of the drive signals. Accordingly, an applied 'motor run' signal 94 in combination with the DC feedback voltage 92 and the time constant of the R and C filter 96, cause the drive circuit 69 to generate drive signals 74, 76 that sweep in frequency from a slightly higher initial frequency that is useful for starting the motor 800 from standstill to an appropriate running frequency that establishes a steady-state motor speed.

Alternatively, the drive signals, 74, 76 for the ultrasonic motor 800 may be generated from combined signals Q1/Q3, and Q2/Q4 through suitable filtering to generate low voltage sinusoidal sine and cosine signals. These signals may then be amplified to sufficient level (typically about 100 Volts RMS) to drive the ultrasonic motor 800.

Figure 15:
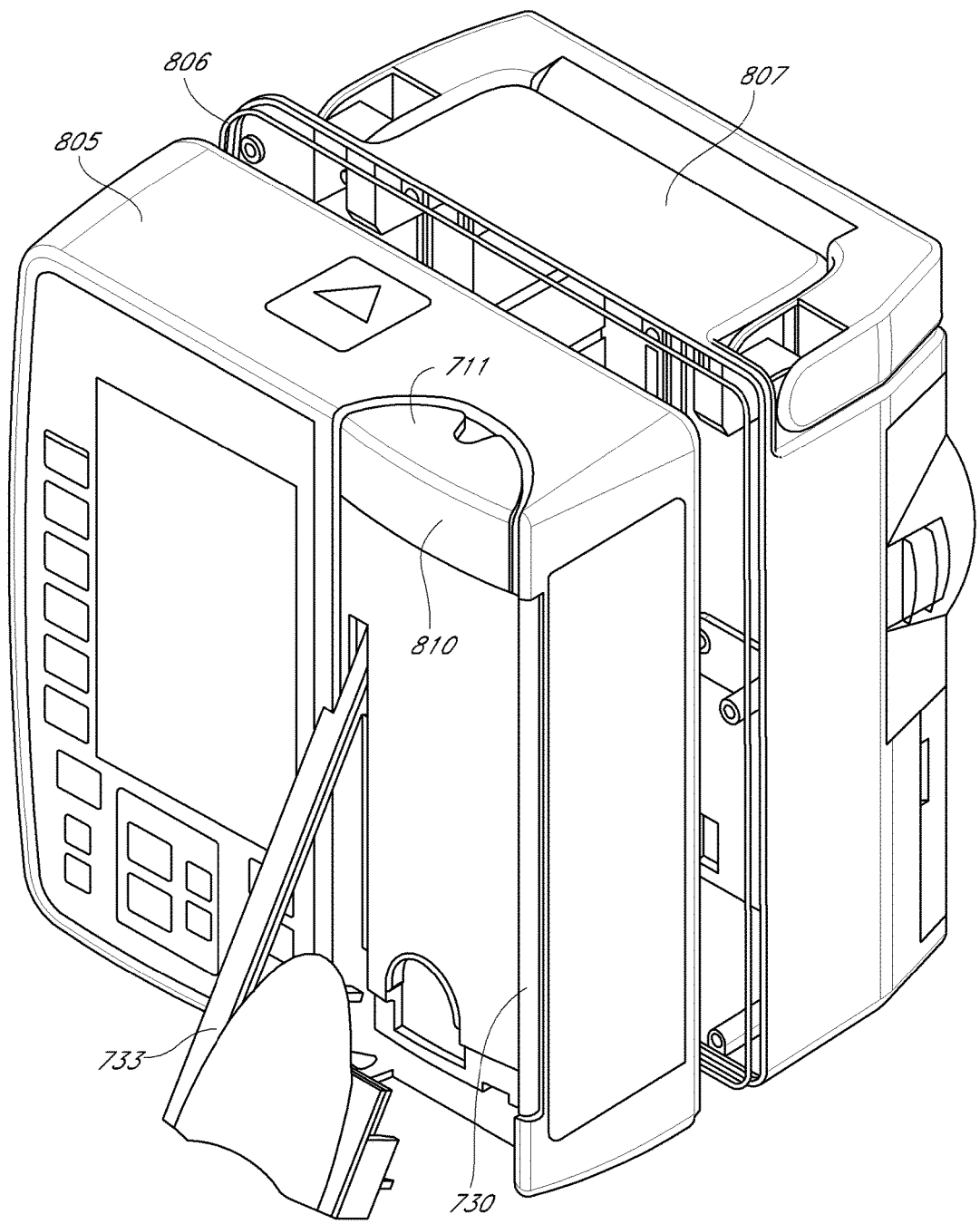
FIG. 15 is an exploded perspective view of a pump unit.
Figure 16:
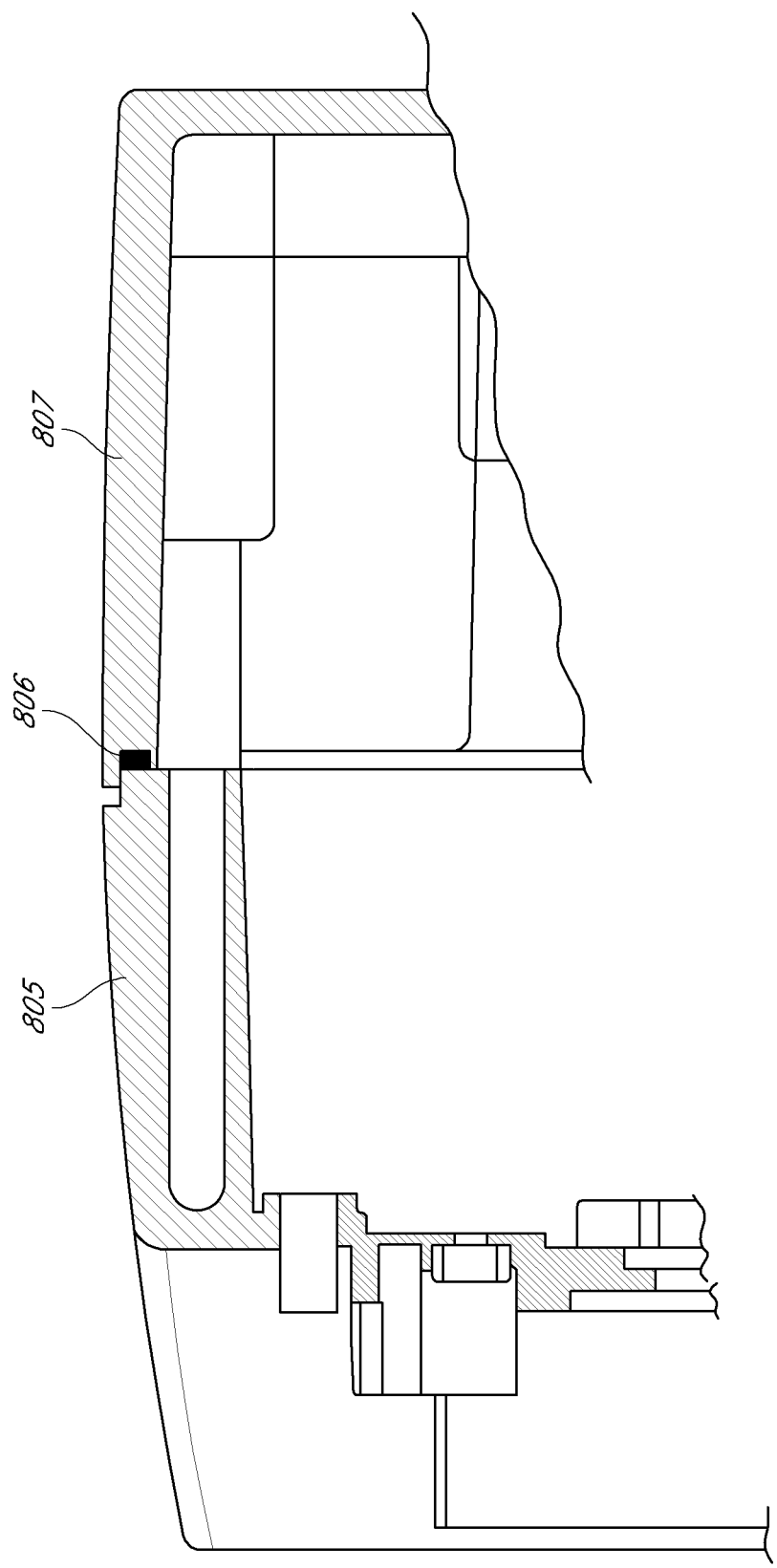
FIG. 16 is a partial sectional view of a gasket disposed between housing segments.

Referring now to FIG. 15, there is shown an exploded perspective view of one embodiment of the pump unit 406 in which a gasket 806 is disposed between mating segments 805, 807 of the housing. The gasket 806 is formed of a flexible and electrically conductive material to form a fluid-tight seal between the housing segments 805, 807 as shown in the sectional view of FIG. 16. The conductive gasket 806 also inhibits internally-generated RF noise signals from radiating out of the conductive housing segments 805, 807. The conductive housing segments 805, 807 thus form an integral shield that prevents radiative electronic signals from emanating from internal circuitry, for example as illustrated in FIGS. 12A-12C, and additionally protects such internal circuitry from fluid spills that might be detrimental to reliable operation.

Figure 17:
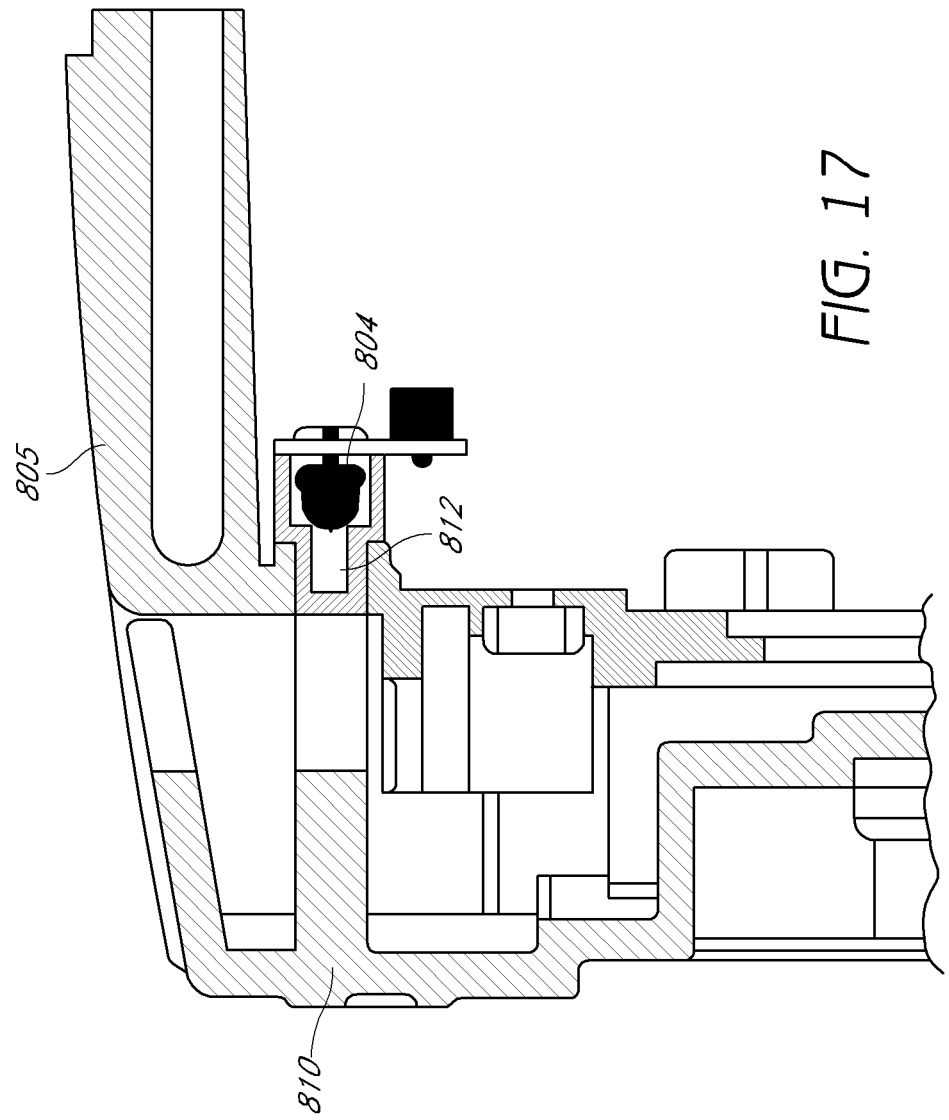
FIG. 17 is a partial cross sectional view of annunciator lights.
Figure 18:
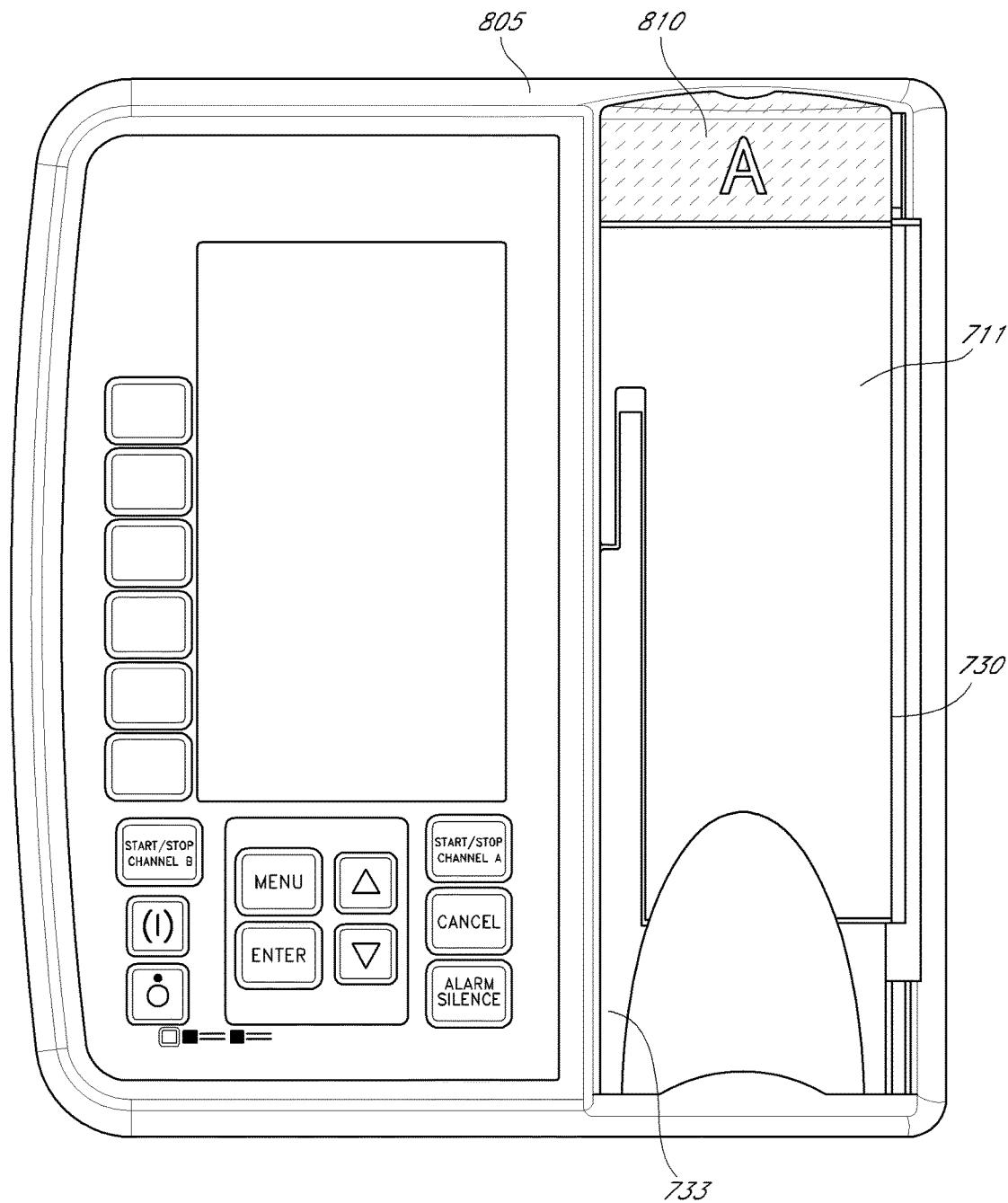
FIG. 18 is a front view of the pump unit of FIG. 15.

Referring now to the sectional view of FIG. 17, there is shown one light source such as light-emitting diode 804 of a plurality of such light sources and different colors that are lineally disposed within the housing segment 805 near a top edge thereof. These light sources are positioned behind the door 711 of conductive material that is hinged 730 along an outer edge of the housing segment 805 to facilitate easy access to the peristaltic pumping structure that is supported therein. The door 711 includes a locking lever 733 for securely closing the door 711 in operational position against a length of tubing 703, as illustrated and previously described herein with reference to FIG. 7. The door 711 also includes a clear or translucent window 810, as illustrated in FIGS. 17, 18, in alignment with the light sources 804 to provide large-area illumination for easy visualization from a distant location of the light from a source 804. A light-scattering element or light pipe 812 may be disposed intermediate the light sources 804 and the window 810 to provide more uniform illumination over the area of the window 810. Thus, a light source 804 of green color may pulse on and off recurring during normal pumping operation, and a light source of red color may pulse on and off recurring to indicate an alarm condition, all for convenient visualization from a distant location. And the light sources 804 are sufficiently recessed within the conductive housing segment 805 to inhibit radiative RF noise signals from emanating from the housing.

Therefore, the liquid infusion apparatus promotes easy replacement or substitution of pumping devices without interrupting patient connection or otherwise comprising sterility of an installed infusion system. An infusion set includes integral segments of a liquid conduit and operable components for interaction and operational engagement with associated components of a pumping device that is compatible with an MRI environment. Ultrasonic motor drive signals are generated with low harmonic content using efficient step-up transformer that co-act with the characteristic input impedance of the ultrasonic motor to shape signals as sinusoidal waveforms of low harmonic content.

In certain embodiments, physiological parameters of a patient may be monitored. Such parameters may include for example, heart rate, respiration rate, blood pressure, blood oxygen saturation, eye response to stimulation and the like. Conventional devices for monitoring these parameters may need to be disconnected as the patient is moved into the MRI suite or hyperbaric chamber. Thus, it may be desirable to integrate these patient monitoring capabilities with a liquid infusion device compatible with an MRI suite and/or hyperbaric chamber.

In certain embodiments, the liquid infusion device 43 may transmit information related to its operation. Such information may include without limitation, pump pressure, current infusion rate settings, current actual or detected infusion rate, general status information, alarm conditions, amount of liquid infused, amount of liquid remaining to be infused, battery power, detected signal strength, and the like. Some or all of this information may be transmitted automatically in a continuous fashion and/or in response to queries received from the controller. The information may be transmitted in a series of packets. The series of packets may follow a prescribed sequence. For example, a first packet may transmit information related to the current infusion rate. A second packet may transmit information related to an amount of liquid infused and so on. The complete series may repeat following a prescribed interval and may be completed for example once per second. Alternatively, the series of packets may be asynchronous.

The liquid infusion device 43 may also transmit information related to one or more physiological parameters as described above. In certain embodiments, one or more high priority physiological parameters may be transmitted with greater frequency than other low priority physiological parameters and/or with greater frequency than the device operation information described above. In certain embodiments, physiological parameter data that is anomalous or indicates a potentially dangerous health situation may be sent with greater priority. Physiological parameter data may be classified as high priority when it falls above or below predetermined thresholds or when it has experienced a rapid change. For example, a physician may wish to monitor a patient's heart beat in substantially real time, e.g., by receiving an audio or visual signal corresponding to each heart beat as it is detected. This may be accomplished by including heart beat information in each packet or in a high percentage of packets. In certain embodiments, each packet will contain a dedicated one or more bits corresponding to heart beat. If a heart beat is currently detected as occurring, the one or more bits may be set to '1'. If no heart beat is currently detected, the one or more bits may be set to '0'. Such substantially real-time monitoring may also be accomplished by generating a new packet when a heart beat is detected.

Figure 19:
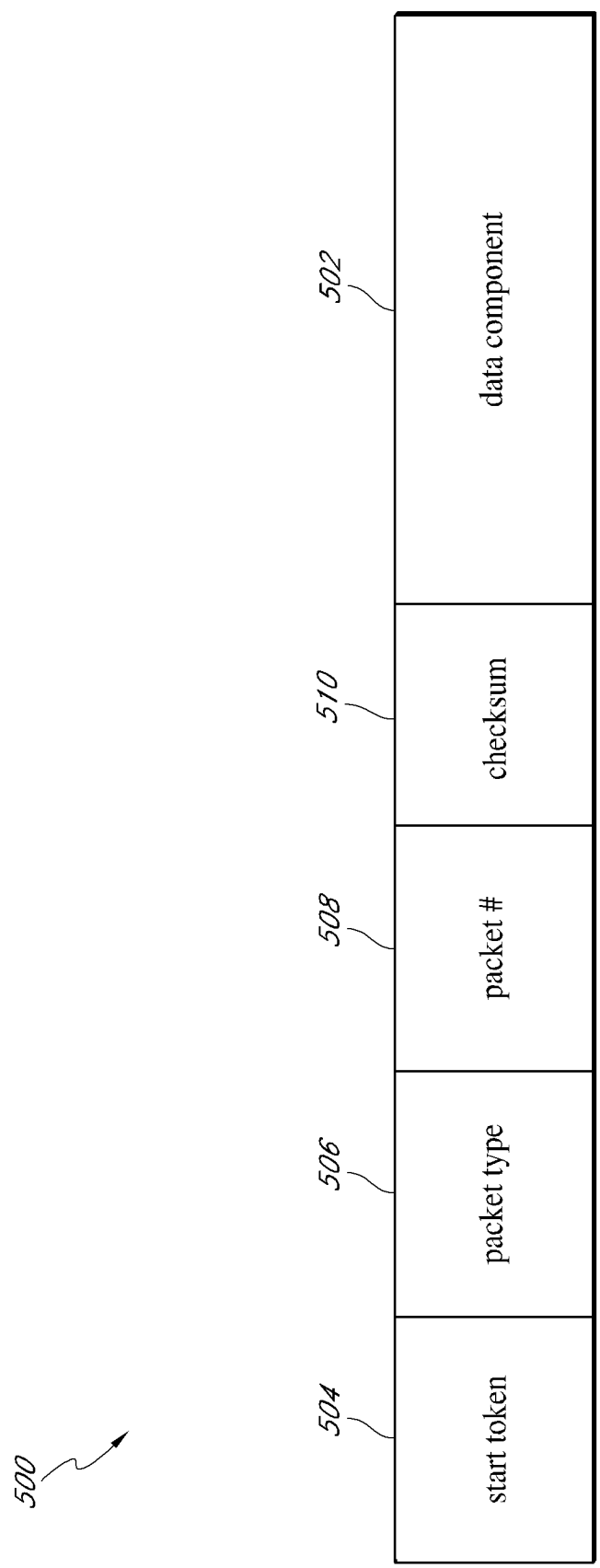
FIG. 19 is an exemplary illustration of an information packet.

As disclosed above, in certain embodiments device and/or physiological parameter data may be sent using packets. The data may be placed inside a packet and sent to the remote. When the remote receives the packet it may determine the packet's validity and the packet's type, and then process the packet data. In certain embodiments, an information packet may contain one or more of the following components: a data component (which may contain, e.g., device data or physiological parameter data), a start token, a packet 'type' indicator token, a packet number, and a checksum component. FIG. 19 illustrates an exemplary embodiment of an information packet 500 with a data component 502 having three bytes. In this exemplary embodiment, the start token 504, packet 'type' indicator token 506, packet number 508, and checksum component 510 may each be a single byte. In certain embodiments, more or less storage may be utilized for various components. In certain embodiments, the infusion device 43 may send information using two different categories of packets. A first packet category (category 1) may be used to send information in a continuous or deterministic stream. In this embodiment, each packet may be assigned an identifier such as a numeric value that indicates that packet's content type. In certain embodiments, the packet types may be identified by numbers starting at 0 and ending at packet N−1, where N is the total number of packet types. In certain embodiments, 61 packet types may be used. In other embodiments, 5 or fewer packet types may be used. In other embodiments, between 6 and 60 packet types may be used. In other embodiments, more than 61 packet types may be used. The remote may be able to predict the packet that it should receive next based on the previous packet's number.

When the pump sends packets to a remote, the pump will send packet type 0, then packet type 1, and so on until the last packet is sent. The process may repeat itself while the infusion pump is running. Packets may also be sent while the infusion pump is not running. Different sequences of packets may be used for various configurations or operating conditions, such as when the infusion pump is operating, when the infusion pump is not operating, or when different physiological parameters are being monitored. Packets may be sent at a guaranteed minimum rate of $R_m$ packets/second (e.g., $R_m$=30 for 30 packets a second.) Packets may be sent faster than the guaranteed minimum rate. When a guaranteed minimum rate of transmission is used, all data at the remote is guaranteed to be completely updated in $N/R_m$ seconds, or when 61 packet types are used, in just over 2 seconds.

When the communication link is compromised, packets begin to be missed and/or contain errors. The remote may determine the validity of a packet by using a checksum operation. One type of checksum operates by adding up the basic components of a message or packet, e.g. the asserted bits, and storing them. The remote or controller receiving the packet performs the same operation on the data and compares the result to the authentic checksum. If the sums match, the remote assumes that the packet was most likely not corrupted. More sophisticated types of redundancy checks that may be used include Fletcher's checksum, Adler-32, and cyclic redundancy checks. Other methods for error detection and/or correction may also be used, such as forward error correcting algorithms and/or turbo coding, automatic repeat request algorithms, Hamming codes, and the like. "Lost" packets may be detected by including a packet number with each packet and sending them in a prescribed sequence. If the remote receives a packet that appears to be out of sequence, e.g. if the remote receives packet number 7 immediately after receiving packet number 5, the remote can determine that the intervening packet was lost.

In certain embodiments, the receiver simply ignores lost or corrupted packets until good packets (e.g. packets passing the checksum or other integrity test) are again received. In other words, the remote may simply wait for the next packet rather than requesting that the missed or corrupted packet be resent. Alternatively, the remote may send a signal to the infusion device 43 requesting that the missed or corrupted packet be resent. In certain embodiments, the infusion device 43 may only request that high-priority packets be resent. If the second attempt also fails, the liquid infusion device 43 may again attempt to resend the packet of high priority data. In certain embodiments, this process may be repeated until a predetermined maximum number of attempts are reached. In certain embodiments, if a certain number of failed attempts are detected, the remote may generate an alarm indicating a problem with the wireless communication.

In certain embodiments, the system may provide a signal integrity indicator. The signal integrity indicator may display an indication of the detected signal strength by, for example, using a plurality of bars similar to those used for cell phones or a number corresponding to signal strength. When packets begin to get lost, the indicator may indicate less signal strength. When the level of bad or lost packets reaches a defined point, the indicator may indicate a "broken" link. The link may be classified as broken when the same packet is missed two or three times in a row. In addition, or alternatively, the link may be classified as broken when a certain number or percentage of the combined packets are missed within a predetermined period of time. The receiver will constantly look for "good" packets and will "re-link" when good packets are again received.

One type of packet may indicate received signal strength information. For example, a packet may have been received correctly, but the signal strength may be low. A packet may be sent indicating that one or more packets were not received correctly or that the received signal strength was low. The received signal strength can be displayed. When a component receives a packet that indicates the received signal strength is low, the component may boost transmission power for future packets. Alternatively, when a component receives a packet indicating high received signal strength, the component may reduce the broadcast strength of future transmissions.

As disclosed above, it may be desirable to send certain information with little delay, and without waiting for a certain packet or for a specific Nth packet's transmission time. Such high priority data can include alarm sounds or messages, new data entered by the operator, detection of a physiological event such as a heart beat, or the state of indicator/status lights such as those corresponding to a patient's real-time heart beat. This information may be sent using a second class of packets (category 2). When these category 2 packets are queued-up to be sent, they are given priority over the sequential, category 1 packets. The transmitter can interleave category 2 packets into the sequential category 1 packets in a substantially immediate manner. The interleaved stream may send one or more category 2 packets between each of the category 1 packets. However, in embodiments with a guaranteed transmission rate, the category 1 packets will not be sent slower than the guaranteed minimum rate of $R_m$ packets/second. Category 2 packets may include a special token or identifier to indicate their status as category 2 packets. Packet types may still be used in category 2 packets to define the data contained.

Figure 20:
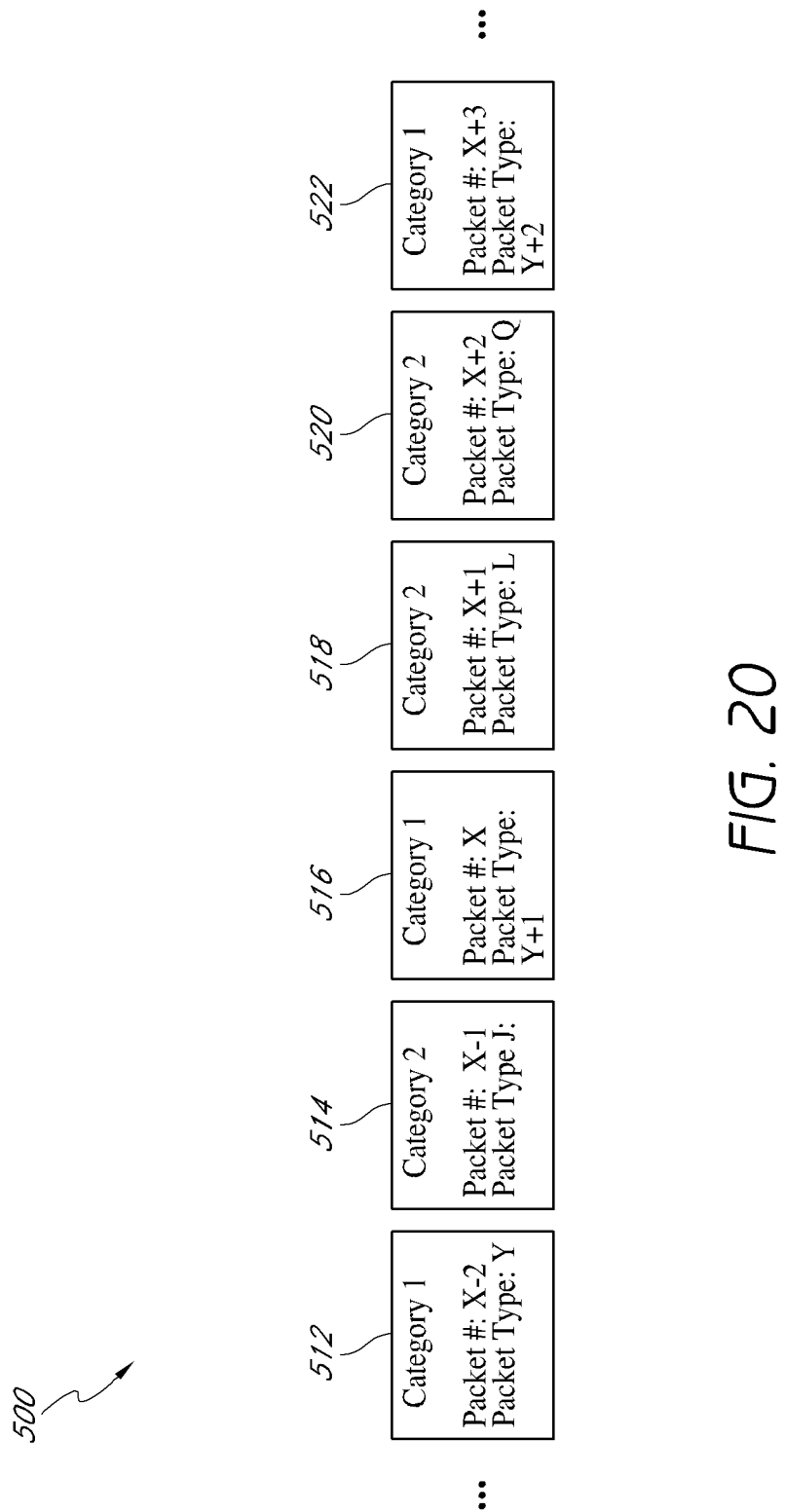
FIG. 20 is an exemplary illustration of the transmission of Category 1 and Category 2 packets.

FIG. 20 illustrates an exemplary transmission sequence of category 1 and category 2 packets. As illustrated, each of the packets 512, 514, 516, 518, and 520 includes a packet number. As described above, the packet numbers may be sequential to assist the remote in ensuring that no packets are lost or corrupted. Three of the illustrated packets 512, 516, and 522 are category 1 packets. A packet's category may be identified by a separate category identifier. Alternatively, a packet's category may be embedded in or derived from the packet type identifier. The category 1 packets follow a prescribed sequence. Thus, packet 512 is identified as a "type Y" packet. Packets 516 and 522 are identified as "type Y+1" and "type Y+2" packets, respectively, indicating a deterministic sequence. Interleaved between the category 1 packets are exemplary category 2 packets, 514, 518, and 520. The category 2 packets do not necessarily follow a prescribed sequence and may be generated and transmitted as the need arises. Accordingly the illustrated category 2 packets' types are identified by letters 'J', 'Q', and signifying the lack of a predefined sequence.

Category 2 packets may be particularly useful where it is desired to monitor a physiological parameter such as a patient's heartbeat in substantially real-time. For example, if the heart rate is 240 beats per minute or 4 beats per second, 8 category 2 "beep" packets should be sent every 2 seconds. Accordingly, if there are 61 category 1 packets to be sent, the "beep" packets would need to be placed in between every $7^{th}$ to $8^{th}$ category 1 packet.

If there is an urgency for transmitting a category 2 packet, the transmission of a category 1 packet could be interrupted, and the interrupted category 1 packet would then be retransmitted after the transmission of the category 2 packet was complete. Alternatively, transmission of the category 2 packet could wait until the transmission is complete for any active category 1 packet. If transmission of the category 2 packet is less urgent, additional category 1 packets could be transmitted prior to the transmission of the category 2 packet. Accordingly, the time required for transmission of a category 2 packet after a triggering event could vary.

For example, the use of category 2 packets may allow a signal indicative of a heart beat to be received by the remote within the time required to transmit the category 2 packet, within the time required to transmit the remainder of a category 1 packet and the category 2 packet, or within the time required to transmit a complete category 1 packet in addition to the remainder of a category 1 packet and the category 2 packet.

In another embodiment, a category 2 packet could be scheduled to follow a particular category 1 packet. Similarly, a category 1 packet could be optional, and may not be transmitted with every sequence.

Given the various embodiments available, category 2 packets may be scheduled, for example, within one second of a triggering event, within half a second of a triggering event, within a tenth of a second of a triggering event, or within one one-hundredth of a second of a triggering event. These times are merely exemplary, and other response times are also possible.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combinations or sub-combinations of the specific features and aspects of the embodiments can be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. A liquid infusion system configured to facilitate wireless communication between a liquid infusion apparatus within a magnetic resonance imaging (MRI) scan room and a remote control outside the MRI scan room, the system comprising:
   a liquid conduit;
   a pump configured to receive the liquid conduit and to transfer a liquid from a liquid source through the liquid conduit in response to activation of the pump;
   a drive motor coupled to the pump to provide mechanical movement to the pump to provide displacement of the liquid from the liquid source through the liquid conduit;
   a controller configured to communicate with the drive motor to drive the pump, thereby transferring liquid from the liquid source through the liquid conduit at a controllable volumetric rate; and a first communication port configured to provide a wireless communication link with a remote control located outside an MRI scan room, wherein the wireless communication link operates within a frequency range that is at least an order of magnitude higher than an operating frequency range of MRI equipment such that the wireless communication link does not interfere with operation of the MRI equipment, wherein the wireless communication link utilizes a selected communication channel from a plurality of configured channels, wherein the pump is configured to operate even if communication with the remote control is interrupted.

2. The liquid infusion system of claim 1, wherein communication using the selected communication channel does not substantially interfere with communications from a liquid infusion apparatus utilizing a second communication channel of the plurality of configured channels.

3. The liquid infusion system of claim 1, wherein the remote control allows for selection by a remote operator of a second communication channel to communicate with a second communication port located separate from the first communication port.

4. The liquid infusion system of claim 1, wherein the wireless communication link utilizes a frequency hopping spread spectrum transceiver.

5. The liquid infusion system of claim 1, wherein the wireless communication link utilizes an industrial, scientific and medical (ISM) radio band.

6. The liquid infusion system of claim 1, wherein the wireless communication link utilizes a Bluetooth protocol.

7. The liquid infusion system of claim 1, wherein the wireless communication link utilizes an infrared transceiver.

8. The liquid infusion system of claim 1, wherein the controller is configured to generate an alarm when there is an interruption of communication over the wireless communication link.

9. The liquid infusion system of claim 1, wherein the controller is configured to generate an alert tone when communication is established over the wireless communication link.

10. The liquid infusion system of claim 1, wherein the controller is configured to generate an output indicative of a connection status of the wireless communication link for display on the remote control.

11. The liquid infusion system of claim 1, wherein the liquid infusion system does not include any ferrous or magnetic materials.

12. The liquid infusion system of claim 1, wherein a display of the remote control mirrors a display of the pump.

13. A liquid infusion system configured to facilitate wireless communication between at least one liquid infusion pump within a magnetic resonance imaging (MRI) scan room and at least one remote control outside the MRI scan room, the system comprising:

a first liquid conduit;

a first pump configured to receive the first liquid conduit and to transfer a first liquid from a first liquid source through the first liquid conduit in response to activation of the first pump;

a first drive motor coupled to provide mechanical movement to the first pump to provide displacement of the first liquid from the first liquid source through the first liquid conduit;

a first sensor configured to provide an indication of a volume of the first liquid displaced through the first liquid conduit;

a first controller configured to communicate with the first sensor to receive the indication of the volume of the first liquid displaced through the first liquid conduit, the first controller further configured to communicate with the first drive motor to drive the first pump, thereby transferring the first liquid from the first liquid source through the first liquid conduit at a controllable volumetric rate;

a second liquid conduit;

a second pump configured to receive the second liquid conduit and to transfer a second liquid from a second liquid source through the second liquid conduit in response to activation of the second pump;

a second drive motor coupled to provide mechanical movement to the second pump to provide displacement of the second liquid from the second liquid source through the second liquid conduit;

a second sensor configured to provide an indication of a volume of the second liquid displaced through the second liquid conduit;

a second controller configured to communicate with the second sensor to receive the indication of the volume of the second liquid displaced through the second liquid conduit, the second controller further configured to communicate with the second drive motor to drive the second pump, thereby transferring the second liquid from the second liquid source through the second liquid conduit at a controllable volumetric rate; and a first communication port configured to provide a first wireless communication link with a remote control located outside an MRI scan room;

a second communication port in the second pump configured to provide a second wireless communication link with the remote control located outside the MRI scan room, wherein the first wireless communication link and the second wireless communication link operate within a frequency range that is at least an order of magnitude higher than an operating frequency range of MRI equipment such that the first wireless communication link and the second wireless communication link do not interfere with operation of the MRI equipment, wherein a first communication channel to be utilized by the first wireless communication link and a second communication channel to be utilized by the second wireless communication link are selectable from a plurality of configured channels.

14. The liquid infusion system of claim 13, wherein at least one of the first and second wireless communication links utilizes a frequency hopping spread spectrum transceiver.

15. The liquid infusion system of claim 13, wherein at least one of the first and second wireless communication links utilizes a Bluetooth protocol.

16. The liquid infusion system of claim 13, wherein at least one of the first and second wireless communication links utilizes an infrared transceiver.

17. The liquid infusion system of claim 13, wherein each of the first controller and the second controller is configured to generate an output indicative of a connection status of the respective wireless communication link for display on the remote control.

18. The liquid infusion system of claim 13, wherein the first pump and the second pump are configured to operate even if communication with the remote control is interrupted.

19. The liquid infusion system of claim 13, wherein the liquid infusion system does not include any ferrous or magnetic materials.

20. The liquid infusion system of claim 13, wherein the remote control is configured to cycle through the plurality of configured channels and provide periodic updates to a remote operator of the status of at least one of the first pump and the second pump.

\* \* \* \* \*